(12) United States Patent
Mercanzini et al.

(10) Patent No.: US 10,702,692 B2
(45) Date of Patent: Jul. 7, 2020

(54) NEUROSTIMULATION DEVICE

(71) Applicant: ALEVA NEUROTHERAPEUTICS, Lausanne (CH)

(72) Inventors: Andre Mercanzini, Saint Sulpice (CH); Zbynek Struzka, Lausanne (CH); Jason Jinyu Ruan, Lausanne (CH); Pascal Harbi, Lausanne (CH); Alain Jordan, Lausanne (CH)

(73) Assignee: ALEVA NEUROTHERAPEUTICS, Lausanne (CH)

( * ) Notice: Subject to any disclaimer, the term of this patent is extended or adjusted under 35 U.S.C. 154(b) by 139 days.

(21) Appl. No.: 15/910,278

(22) Filed: Mar. 2, 2018

(65) Prior Publication Data

US 2019/0269906 A1 Sep. 5, 2019

(51) Int. Cl.
*A61N 1/05* (2006.01)
*A61N 1/36* (2006.01)
*A61B 90/00* (2016.01)

(52) U.S. Cl.
CPC ......... *A61N 1/0539* (2013.01); *A61N 1/0534* (2013.01); *A61N 1/0551* (2013.01); *A61N 1/3605* (2013.01); *A61B 2090/3966* (2016.02)

(58) Field of Classification Search
CPC combination set(s) only.
See application file for complete search history.

(56) References Cited

U.S. PATENT DOCUMENTS

| | | |
|---|---|---|
| 5,095,905 A | 3/1992 | Klepinski |
| 5,458,629 A | 10/1995 | Baudino et al. |
| 6,301,492 B1 | 10/2001 | Zonenshayn |
| 6,459,936 B2 | 10/2002 | Fischell et al. |
| 6,510,347 B2 | 1/2003 | Borkan |
| 6,581,046 B1 | 6/2003 | Ahissar |
| 7,198,626 B2 | 4/2007 | Lee et al. |
| 7,403,820 B2 | 7/2008 | Dilorenzo |
| 7,684,866 B2 | 3/2010 | Fowler et al. |
| 7,765,012 B2 | 7/2010 | Gerber |
| 7,769,472 B2 | 8/2010 | Gerber |
| 7,822,482 B2 | 10/2010 | Gerber |
| 7,945,329 B2 | 5/2011 | Bedenbaugh |
| 7,991,481 B2 | 8/2011 | Benabid et al. |
| 8,010,202 B2 | 8/2011 | Shah et al. |
| 8,024,022 B2 | 9/2011 | Schulman et al. |

(Continued)

FOREIGN PATENT DOCUMENTS

| | | |
|---|---|---|
| CN | 101600470 A | 12/2009 |
| CN | 102274074 A | 12/2011 |

(Continued)

OTHER PUBLICATIONS

Final Office Action on U.S. Appl. No. 15/369,766 dated Feb. 23, 2018.

(Continued)

*Primary Examiner* — Paula J Stice
(74) *Attorney, Agent, or Firm* — Foley & Lardner LLP; James De Vellis

(57) ABSTRACT

The present disclosure describes an implantable lead device that includes an internal support comb. The support comb can include one or more faces that enable the alignment, routing, and holding of the lead device's internal wires. The support comb can enable the interconnection of the wires with to the microelectrode film that includes the lead device's electrodes.

20 Claims, 22 Drawing Sheets

(56) References Cited

U.S. PATENT DOCUMENTS

| | | |
|---|---|---|
| 8,090,450 B2 | 1/2012 | Swoyer et al. |
| 8,108,049 B2 | 1/2012 | King |
| 8,121,702 B2 | 2/2012 | King |
| 8,170,676 B2 | 5/2012 | Greenberg et al. |
| 8,171,621 B2 | 5/2012 | Swanson et al. |
| 8,224,417 B2 | 7/2012 | Vetter |
| 8,224,462 B2 | 7/2012 | Westlund et al. |
| 8,244,377 B1 | 8/2012 | Pianca et al. |
| 8,271,094 B1 | 9/2012 | Moffitt et al. |
| 8,295,943 B2 | 10/2012 | Eggen et al. |
| 8,315,686 B2 | 11/2012 | Llinas et al. |
| 8,321,025 B2 | 11/2012 | Bedenbaugh |
| 8,332,046 B2 | 12/2012 | Anderson et al. |
| 8,374,703 B2 | 2/2013 | Imran |
| 8,463,353 B2 | 6/2013 | Seymour |
| 8,463,398 B2 | 6/2013 | Jackson et al. |
| 8,467,877 B2 | 6/2013 | Imran |
| 8,509,872 B2 | 8/2013 | Lee et al. |
| 8,509,876 B2 | 8/2013 | Karmarkar |
| 8,509,920 B2 | 8/2013 | Wahlstrand et al. |
| 8,560,085 B2 | 10/2013 | Moffitt et al. |
| 8,565,894 B2 | 10/2013 | Vetter et al. |
| 8,571,665 B2 | 10/2013 | Moffitt et al. |
| 8,583,253 B1 | 11/2013 | Shi et al. |
| 8,620,452 B2 | 12/2013 | King et al. |
| 8,626,312 B2 | 1/2014 | King et al. |
| 8,634,934 B2 | 1/2014 | Kokones et al. |
| 8,644,903 B1 | 2/2014 | Osa et al. |
| 8,649,879 B2 | 2/2014 | Digiore et al. |
| 8,666,509 B2 | 3/2014 | Howard et al. |
| 8,694,105 B2 | 4/2014 | Martens et al. |
| 8,694,123 B2 | 4/2014 | Wahlstrand et al. |
| 8,694,127 B2 | 4/2014 | Pianca et al. |
| 8,731,673 B2 | 5/2014 | Vetter et al. |
| 8,738,154 B2 | 5/2014 | Zdeblick et al. |
| 8,744,596 B2 | 6/2014 | Howard |
| 8,755,906 B2 | 6/2014 | Moffitt et al. |
| 8,762,065 B2 | 6/2014 | Dilorenzo |
| 8,774,891 B1 | 7/2014 | Osa et al. |
| 8,788,056 B2 | 7/2014 | King et al. |
| 8,788,063 B2 | 7/2014 | Chen |
| 8,792,993 B2 | 7/2014 | Pianca et al. |
| 8,800,140 B2 | 8/2014 | Hetke et al. |
| 8,825,175 B2 | 9/2014 | King |
| 8,831,739 B2 | 9/2014 | McCreery et al. |
| 8,831,742 B2 | 9/2014 | Pianca et al. |
| 8,849,369 B2 | 9/2014 | Cogan et al. |
| 8,849,415 B2 | 9/2014 | Bedenbaugh |
| 8,862,242 B2 | 10/2014 | Pianca |
| 8,875,391 B2 | 11/2014 | Pianca et al. |
| 8,923,982 B2 | 12/2014 | Howard |
| 8,934,965 B2 | 1/2015 | Rogers et al. |
| 8,934,980 B2 | 1/2015 | Pless et al. |
| 8,938,300 B2 | 1/2015 | Rosero |
| 8,958,862 B2 | 2/2015 | Hetke et al. |
| 8,968,331 B1 | 3/2015 | Sochor |
| 8,977,335 B2 | 3/2015 | Putz |
| 8,977,367 B2 | 3/2015 | Elahi et al. |
| 8,989,864 B2 | 3/2015 | Funderburk et al. |
| 9,008,747 B2 | 4/2015 | Seymour et al. |
| 9,014,796 B2 | 4/2015 | Kipke et al. |
| 9,044,590 B2 | 6/2015 | Greenberg et al. |
| 9,061,134 B2 | 6/2015 | Askin et al. |
| 9,079,013 B2 | 7/2015 | Digiore et al. |
| 9,089,689 B2 | 7/2015 | Govea |
| 9,089,690 B2 | 7/2015 | Greenberg et al. |
| 9,095,267 B2 | 8/2015 | Halpern et al. |
| 9,149,630 B2 | 10/2015 | Howard et al. |
| 9,211,401 B2 | 12/2015 | Frewin et al. |
| 9,211,402 B2 | 12/2015 | Moffitt et al. |
| 9,220,897 B2 | 12/2015 | Perryman et al. |
| 9,227,050 B2 | 1/2016 | Romero |
| 9,248,272 B2 | 2/2016 | Romero |
| 9,248,275 B2 | 2/2016 | Digiore et al. |
| 9,265,465 B2 | 2/2016 | Najafi et al. |
| 9,265,928 B2 | 2/2016 | Pellinen et al. |
| 9,283,375 B2 | 3/2016 | Moffitt et al. |
| 9,289,151 B2 | 3/2016 | Kipke et al. |
| 9,289,596 B2 | 3/2016 | Leven |
| 9,295,830 B2 | 3/2016 | Pianca |
| 9,314,614 B2 | 4/2016 | Bedenbaugh |
| 9,358,398 B2 | 6/2016 | Moffitt et al. |
| 9,364,659 B1 | 6/2016 | Rao |
| 9,381,347 B2 | 7/2016 | Howard et al. |
| 9,381,348 B2 | 7/2016 | Romero et al. |
| 9,381,356 B2 | 7/2016 | Parker et al. |
| 9,399,128 B2 | 7/2016 | Tooker et al. |
| 9,427,567 B2 | 8/2016 | Romero |
| 9,440,082 B2 | 9/2016 | Mercanzini et al. |
| 9,474,895 B2 | 10/2016 | Digiore et al. |
| 9,498,620 B2 | 11/2016 | Romero et al. |
| 9,517,020 B2 | 12/2016 | Shacham-Diamand et al. |
| 9,592,377 B2 | 3/2017 | Greenberg et al. |
| 9,604,051 B2 | 3/2017 | Vetter et al. |
| 9,662,494 B2 | 5/2017 | Young |
| 9,700,715 B2 | 7/2017 | Dou |
| 9,743,878 B2 | 8/2017 | Drew |
| 9,775,983 B2 | 10/2017 | Digiore et al. |
| 9,775,988 B2 | 10/2017 | Govea et al. |
| 9,827,413 B2 | 11/2017 | Barker et al. |
| 9,833,611 B2 | 12/2017 | Govea et al. |
| 9,855,428 B2 | 1/2018 | Henry et al. |
| 9,861,288 B2 | 1/2018 | Ma et al. |
| 9,925,368 B2 | 3/2018 | Ryu et al. |
| 10,046,165 B2 | 8/2018 | Frewin et al. |
| 2001/0051802 A1 | 12/2001 | Woloszko et al. |
| 2001/0051819 A1 | 12/2001 | Fischell et al. |
| 2002/0116042 A1 | 8/2002 | Boling |
| 2005/0171522 A1 | 8/2005 | Christopherson |
| 2006/0084965 A1 | 4/2006 | Young |
| 2006/0095029 A1 | 5/2006 | Young et al. |
| 2006/0184060 A1 | 8/2006 | Belalcazar et al. |
| 2009/0248122 A1 | 10/2009 | Pianca |
| 2010/0047376 A1 | 2/2010 | Imbeau et al. |
| 2014/0277284 A1 | 9/2014 | Chen et al. |
| 2015/0051678 A1 | 2/2015 | Reed et al. |
| 2015/0105774 A1 | 4/2015 | Lindquist et al. |
| 2015/0142090 A1 | 5/2015 | Duijsens et al. |
| 2015/0151111 A1 | 6/2015 | Pianca et al. |
| 2015/0209578 A1 | 7/2015 | Kast et al. |
| 2015/0290452 A1 | 10/2015 | Kokones et al. |
| 2015/0335258 A1 | 11/2015 | Masmanidis |
| 2015/0355413 A1 | 12/2015 | Bhagavatula et al. |
| 2015/0360023 A1 | 12/2015 | Howard et al. |
| 2016/0008592 A1 | 1/2016 | Romero et al. |
| 2016/0023003 A1 | 1/2016 | Perryman et al. |
| 2016/0074651 A1 | 3/2016 | Moffitt et al. |
| 2016/0228706 A1 | 8/2016 | Hershey et al. |
| 2016/0331953 A1 | 11/2016 | Reed et al. |
| 2016/0331975 A1 | 11/2016 | Henry et al. |
| 2016/0361535 A1 | 12/2016 | Perryman et al. |
| 2017/0007813 A1 | 1/2017 | Negi et al. |
| 2017/0049345 A1 | 2/2017 | Single |
| 2017/0136238 A1 | 5/2017 | Hartig et al. |
| 2017/0143982 A1 | 5/2017 | Mercanzini |
| 2017/0197086 A1 | 7/2017 | Howard et al. |
| 2017/0266432 A1 | 9/2017 | Seeley et al. |
| 2017/0296808 A1 | 10/2017 | Greenberg et al. |
| 2017/0361101 A1 | 12/2017 | Single |
| 2018/0185656 A1 | 7/2018 | Shepard et al. |

FOREIGN PATENT DOCUMENTS

| | | |
|---|---|---|
| CN | 102341036 A | 2/2012 |
| EP | 0 586 664 A1 | 3/1994 |
| EP | 2 144 665 A1 | 1/2010 |
| EP | 2 389 975 B1 | 11/2011 |
| EP | 2 476 453 A1 | 7/2012 |
| EP | 2 618 889 | 7/2013 |
| EP | 2 664 354 B1 | 11/2013 |
| EP | 2 862 595 B1 | 4/2015 |
| EP | 3 111 835 A1 | 1/2017 |
| EP | 3 231 476 A1 | 10/2017 |
| JP | 2005-052647 | 3/2005 |

(56) References Cited

FOREIGN PATENT DOCUMENTS

| JP | 2012-179333 A | 9/2012 |
|---|---|---|
| WO | WO-2004/043536 A1 | 5/2004 |
| WO | WO-2018/068013 A1 | 5/2004 |
| WO | WO-2008/088897 | 7/2008 |
| WO | WO-2011/000791 A1 | 1/2011 |

OTHER PUBLICATIONS

Non-Final Office Action on U.S. Appl. No. 15/369,766 dated Jun. 29, 2018.
Office Action on U.S. Appl. No. 15/185,709 dated Jul. 3, 2018.
U.S. Notice of Allowance on U.S. Appl. No. 14/731,296 dated May 7, 2018.
Bucher et al., "Low-impedance thin-film polycrystalline silicon microelectrodes for extracellular stimulation and recording", Biosensors & Bioelectronics, vol. 14, 1999, pp. 639-649 (11 pages).
European Search Report on EP 16190439 dated Jul. 19, 2017 (2 pages).
Extended European Search Report on EP 19165102.5 dated Jul. 8, 2019 (7 pages).
Final Office Action on U.S. Appl. No. 16/015,625 dated Dec. 28, 2018 (13 pages).
Hosp et al., "Thin-film epidural microelectrode arrays for somatosensory and motor cortex mapping in rat", Journal of Neuroscience Methods, vol. 172, 2008, pp. 255-262 (8 pages).
International Search Report and Written Opinion of the International Searching Authority on PCT/IB2019/051635 dated Jun. 3, 2019 (13 pages).
International Search Report and Written Opinion of the International Searching Authority on PCT/IB2019/053275 dated Jul. 4, 2019 (12 pages).
Janders et al., "Novel Thin Film Titanium Nitride Micro-Electrodes With Excellent Charge Transfer Capability for Cell Stimulation and Sensing Applications", 18th Annual International Conference of the IEEE Engineering in Medicine and Biology Society, 1996, Amsterdam (3 pages).
Moxon et al., "Nanostructured Surface Modification of Ceramic-Based Microelectrodes to Enhance Biocompatibility for a Direct Brain-Machine Interface", IEEE Transactions on Biomedical Engineering, vol. 51, No. 6, Jun. 2004, pp. 881-889 (9 pages).
Non-Final Office Action on U.S. Appl. No. 15/369,766 dated May 31, 2019 (10 pages).
Non-Final Office Action on U.S. Appl. No. 16/015,625 dated Aug. 9, 2018 (14 pages).
Notice of Allowance on U.S. Appl. No. 15/185,709 dated Jun. 10, 2019 (2 pages).
Notice of Allowance on U.S. Appl. No. 15/281,468 dated Jul. 27, 2018 (2 pages).
Notice of Allowance on U.S. Appl. No. 16/015,625 dated Mar. 28, 2019 (8 pages).
Notice of Allowance on U.S. Appl. No. 16/015,625 dated May 8, 2019 (8 pages).
Notice of Reasons for Rejection on JP 2017-530450 dated Jul. 11, 2019 (4 pages).
Office Action on CN 201580016170.1 dated Jan. 28, 2019 (10 pages).
Ziaie et al., "A Single-Channel Implantable Microstimulator for Functional Neuromuscular Stimulation", IEEE Transactions on Biomedical Engineering, vol. 44, No. 10, Oct. 1997, pp. 909-920 (12 pages).
Notice of Allowance on U.S. Appl. No. 15/185,709 dated Apr. 26, 2019.
Extended European Search Report for EP Application No. 18208814.6 dated Mar. 28, 2019.
Final Office Action on U.S. Appl. No. 15/369,766 dated Feb. 7, 2019.
International Preliminary Report on Patentability and Written Opinion for PCT/IB2017/050551 dated Aug. 16, 2018.
Notice of Allowance on U.S. Appl. No. 14/731,296 dated Aug. 15, 2018.
Notice of Allowance on U.S. Appl. No. 15/185,709 dated Nov. 9, 2018.
Notice of Allowance on U.S. Appl. No. 15/281,468 dated Jun. 1, 2018.
Notice of Allowance on U.S. Appl. No. 15/878,066 dated Oct. 3, 2018.
Notice of Allowance on U.S. Appl. No. 15/878,066 dated Dec. 5, 2018.
Office Action for CA Application No. 2,795,159 dated Dec. 18, 2018.
Office Action for Chinese Application No. 201580016170.1 dated Jan. 28, 2019.
Extended European Search Report for EP 19174013.3 dated Oct. 8, 2019 (7 pages).
Notice of Allowance for U.S. Appl. No. 15/369,766 dated Oct. 17, 2019 (12 pages).
First Office Action for CN 201580019701.2 dated Nov. 15, 2019 (18 pages).
Non-Final Office Action for U.S. Appl. No. 15/311,082 dated Jan. 10, 2020 (14 pages).
Office Action for CA 3026948 dated Jan. 15, 2020 (4 pages).

NEUROSTIMULATION DEVICE

BACKGROUND OF THE DISCLOSURE

Deep brain stimulation (DBS) can include neurostimulation therapy that involves electrical stimulation systems that stimulate the human brain and body. DBS can be used to treat a number of neurological disorders. DBS can involve electrically stimulating a target area of the brain.

SUMMARY OF THE DISCLOSURE

The present disclosure describes a stimulation device that can be formed into a cylindrical shape. Internally, the stimulation device can include a silicon etched support comb with faces to align, route, and hold wires. The support comb can enable the interconnection of the wires with the microelectrode film that includes the stimulation device's electrodes. The stimulation device can also include an internal support tube that can reduce mechanical detachment of the microelectrode film from its epoxy mold by providing a long edge anchoring system. The microelectrode film can be rolled into a three-dimensional configuration to increase the degrees of freedom during the assembly process.

According to at least one aspect of the disclosure an implantable lead device can include a support comb. The support comb can include an attachment face and a routing face. The routing face can include a plurality of slots. The lead device can include a microelectrode film. The microelectrode film can include a body. The body can include a plurality of electrodes. The microelectrode film can include an extension extending from the body. The extension can include a first face. The first face of the extension can include a plurality of electrical contacts coupled with the plurality of electrodes. The extension can include a second face. The second face of the extension can be coupled with the attachment face of the support comb. The lead device can include a plurality of wires. Each of the plurality of wires can pass through a respective one of the plurality of slots and couple with a respective one of the plurality of electrical contacts.

The attachment face can include a channel to route an adhesive under at least a portion of the second face of the microelectrode film. A first face of the body of the microelectrode film can be coupled with the support tube. The support tube can include a plurality of radio opaque markers that can be aligned with the plurality of electrodes. The support tube can include a plurality of merlons on a first end. The first end can be configured to mate with or receive the support comb.

The lead device can include a support tube that can include a plurality of radio opaque markers. Each of the plurality of wires can be coupled with a respective one of the plurality of electrical contacts via wire bonding.

The extension of the microelectrode film can include a first leg and a second leg. The first leg can include the first face of the extension and the second face of the extension. The second leg can include a plurality of traces coupling a subset of the plurality of electrodes to the plurality of electrical contacts.

The first leg and the second leg of the extension can be rolled around the support comb. The lead device can include an epoxy backfill of the microelectrode film to form a probe shaft.

According to at least one aspect of the disclosure, a method to manufacture an implantable lead device can include providing a support comb. The support comb can include an attachment face and a routing face. The routing face can include a plurality of slots. The method can include coupling a first portion of a microelectrode film with the attachment face of the support comb. The first portion of the microelectrode film can include a plurality of electrical contacts. The method can include positioning each of a plurality of wires through a respective one of the plurality of slots of the routing face. The method can include coupling each of the plurality of wires with a respective one of the plurality of electrical contacts. The method can include rolling a second portion of the microelectrode film about the support comb.

The method can include forming a second portion of the microelectrode film. The second portion can include a plurality of electrodes in electrical communication with the plurality of electrical contacts. The method can include forming a third portion of the microelectrode film. The third portion can include a plurality of electrical traces coupling a portion of the plurality of electrodes to a portion of the plurality of electrical contacts.

The method can include coupling a second portion of the microelectrode film to an outer face of a support tube. The second portion of the microelectrode film can include a plurality of electrodes. The method can include over molding the support comb with an epoxy.

The method can include forming a plurality of radio opaque markers in a support tube. The method can include aligning the plurality of radio opaque markers with a plurality of electrodes formed in the microelectrode film. The plurality of radio opaque markers can be offset from the plurality of electrodes.

The method can include wire bonding each of the plurality of wires with the respective one of the plurality of electrical contacts. The method can include rolling a second portion of the microelectrode film to form a cylinder. The method can include filling the cylinder with an epoxy.

The method can include under filling a channel formed in the attachment face with an epoxy to couple the first portion of the microelectrode film with the attachment face. The method can include etching the support comb in silicon.

The method can include coupling a first edge of the microelectrode film with a second edge of the microelectrode film to form a cylinder. The method can include inserting the first and second edges of the microelectrode film into a slit of a support tube.

BRIEF DESCRIPTION OF THE DRAWINGS

The accompanying drawings are not intended to be drawn to scale. Like reference numbers and designations in the various drawings indicate like elements. For purposes of clarity, not every component may be labeled in every drawing. In the drawings.

DETAILED DESCRIPTION

The various concepts introduced above and discussed in greater detail below may be implemented in any of numerous ways, as the described concepts are not limited to any particular manner of implementation. Examples of specific implementations and applications are provided primarily for illustrative purposes.

Figure 1:
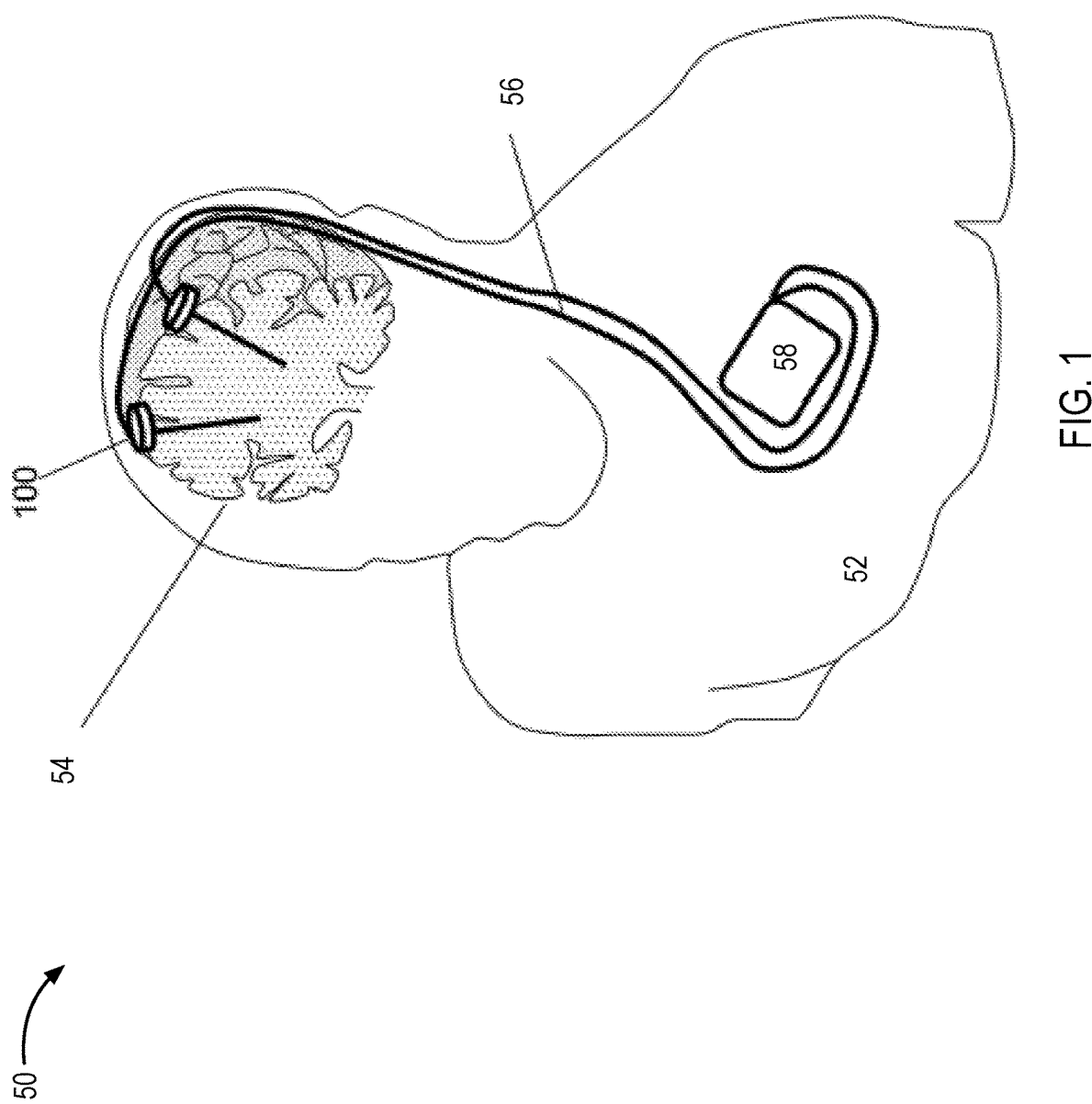
FIG. 1 illustrates an example system to perform neurostimulation.

FIG. 1 illustrates an example system 50 for performing neurostimulation. The system 50 includes a stimulation lead 100 implanted into the brain 54 of a patient 52. The stimulation lead 100 is coupled with a stimulator 58 through cables 56. The stimulator 58 generates therapeutic, electrical stimulations that can be delivered to the patient's brain 54 by the stimulation lead 100. The stimulation lead 100 can be an implantable lead device, which can be chronically or acutely implanted into the patient 52.

Figure 2:
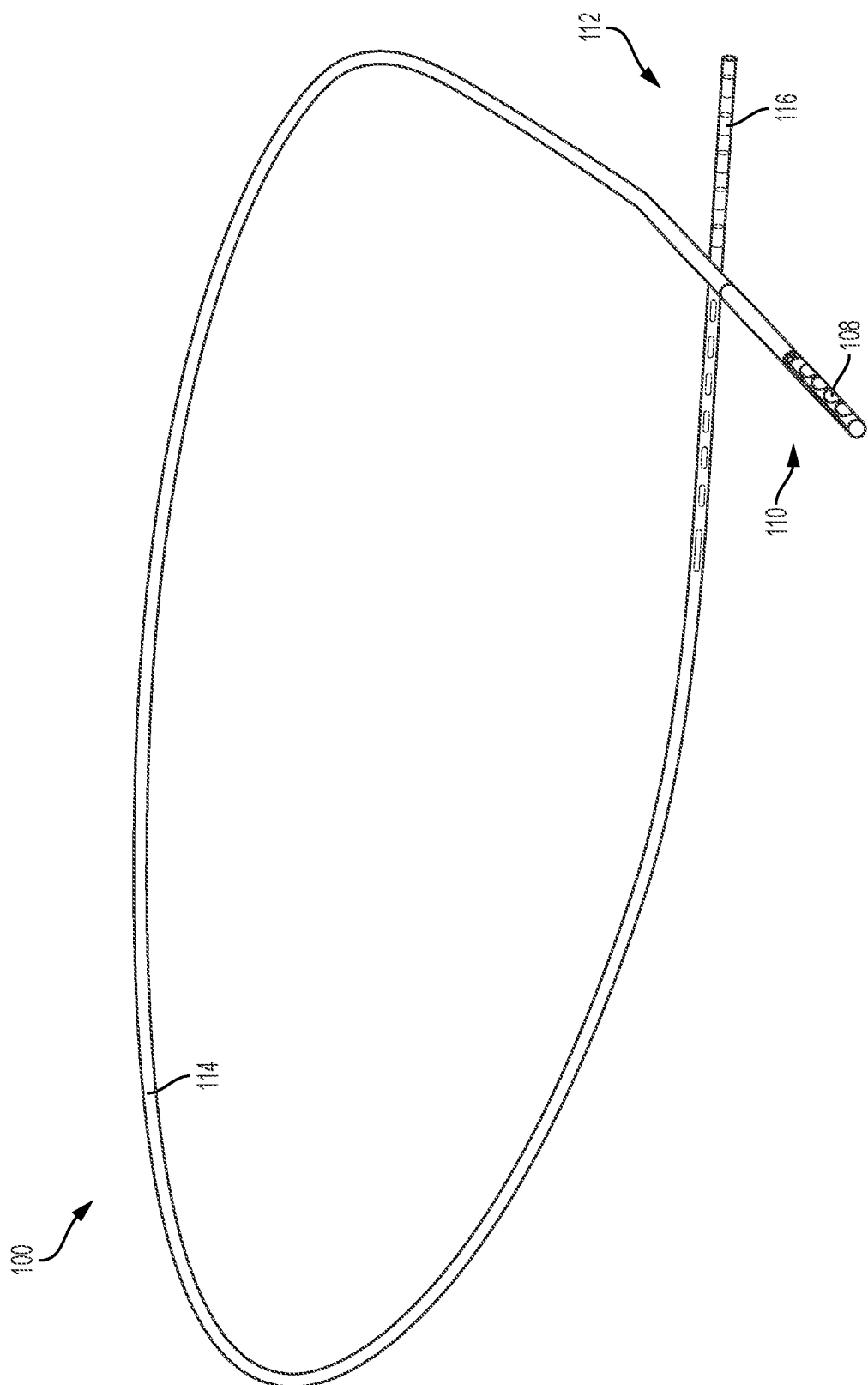
FIG. 2 illustrates the stimulation lead for use in the system illustrated in FIG. 1.

FIG. 2 illustrates the stimulation lead 100. The stimulation lead 100 includes a distal end 110 and a proximal end 112. The distal end 110 includes a plurality of electrodes 108. The proximal end 112 includes a plurality of terminal contacts 116. Each of the terminal contacts 116 are electrically coupled with at least one of the electrodes 108. For example, a wire (or other electrical trace) can run through the interior of the body 114 from one of the terminal contacts 116 to a contact disposed toward the distal end 110 that is in electrical communication with the electrode 108.

Figure 3:
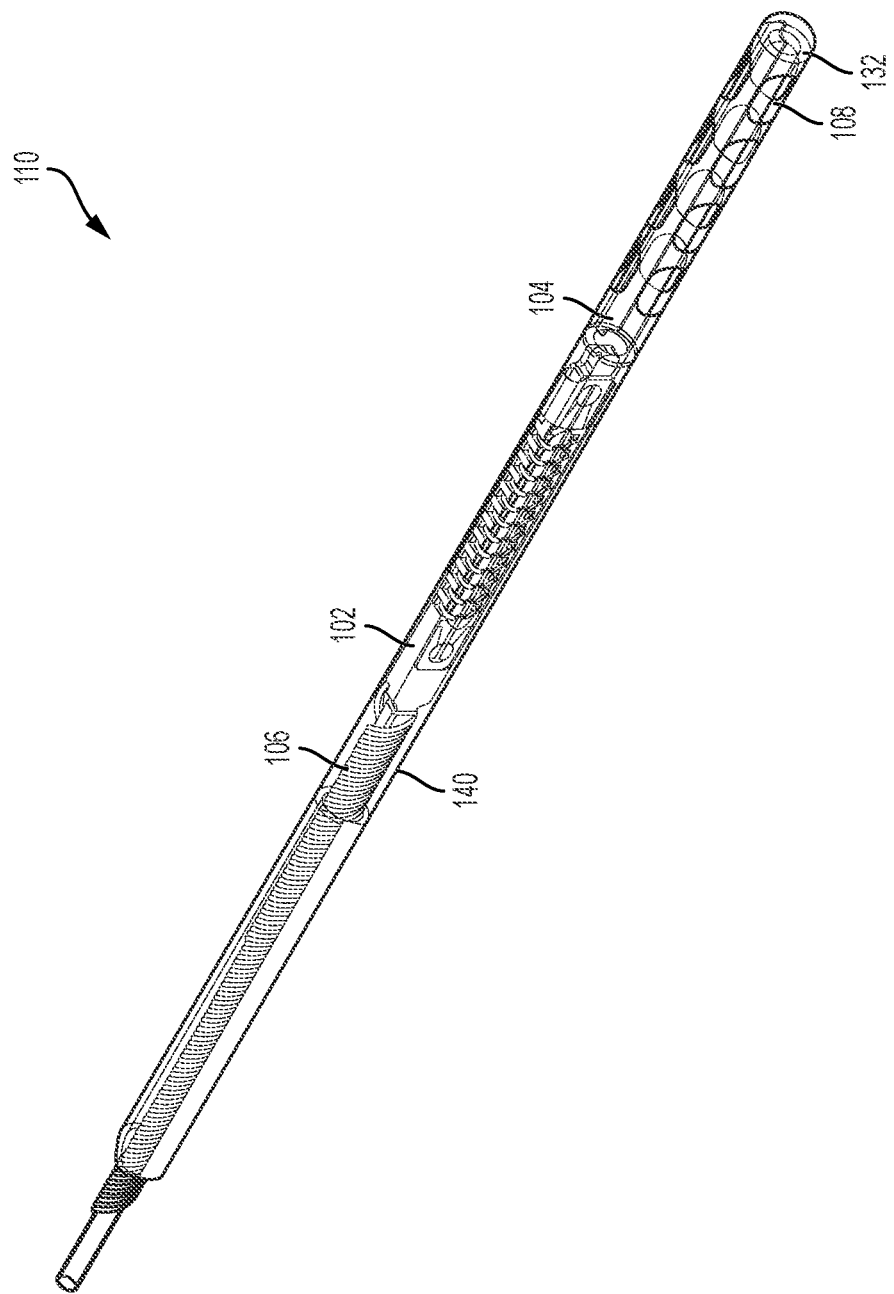
FIG. 3 illustrates a perspective view of the distal end of the stimulation lead illustrated in FIG. 2.

FIG. 3 illustrates a perspective view of the distal end 110 of the stimulation lead 100. As an overview, the distal end 110 includes a microelectrode film 104 with a plurality of electrodes 108. The microelectrode film 104 is coupled with a support tube 132. The distal end 110 also includes the support comb 102. The support comb 102 can enable the attachment of the wires 106 to the microelectrode film 104. The distal end 110 also includes a probe shaft 140. Components of the distal end 110 are described below in connection to FIGS. 4-9, among others, and the assembled distal end 110 is further described in connection to FIGS. 10-17, among others.

Figure 4:
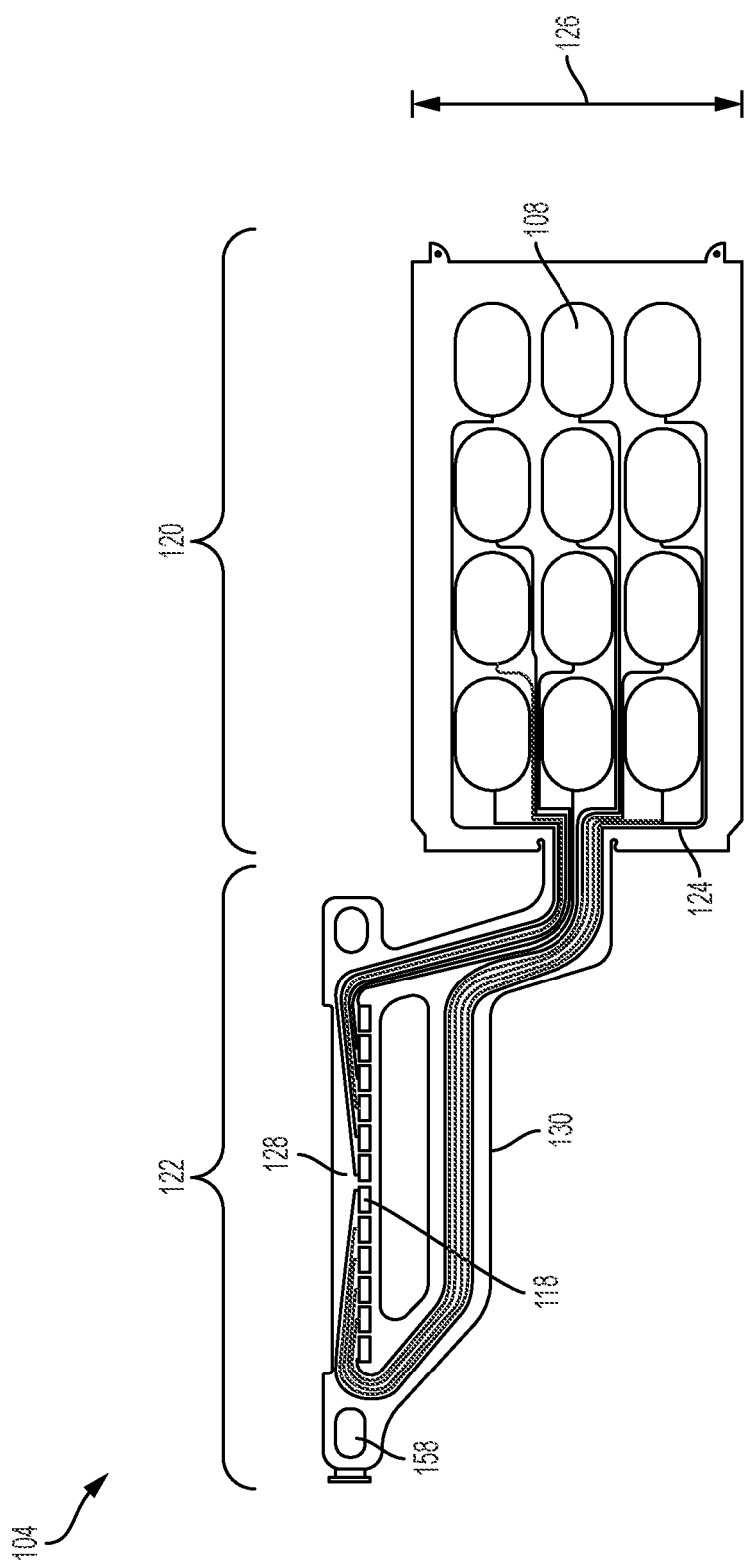
FIG. 4 illustrates a top view of the microelectrode film for use in the stimulation lead illustrated in FIG. 2.

The distal end 110 includes a microelectrode film 104. FIG. 4 illustrates a top view of the microelectrode film 104. FIG. 4 illustrates the microelectrode film 104 in a planar configuration. The microelectrode film 104 includes a body 120 and an extension 122. The body 120 includes a plurality of electrodes 108. The extension 122 includes a plurality of contacts 118. The contacts 118 can be coupled with the electrodes 108 via traces 124.

Figure 5:
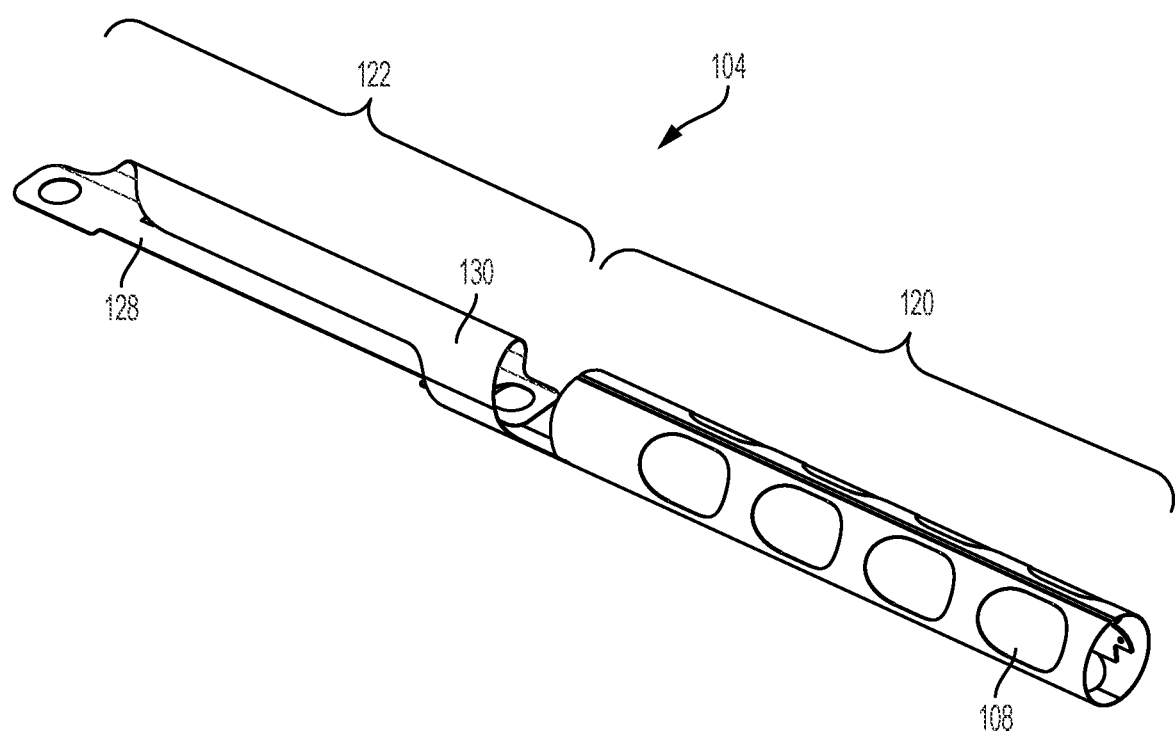
FIG. 5 illustrates the microelectrode film in a rolled configuration.

The microelectrode film 104 includes the body 120. The body 120 can include a plurality of electrodes 108. The body 120 can include between about 4 and about 64, between about 8 and about 32, between about 8 and about 24, or between about 4 and about 12 electrodes 108. The electrodes 108 can be configured as directional or omnidirectional electrodes. For example, in an omnidirectional configuration, the electrode 108 can extend substantially the height 126 of the body 120, such that the electrode 108 wraps substantially around (e.g., at least 80%, or at least 90%) the circumference of the distal end 110 when the microelectrode film 104 is formed into a cylinder (as illustrated in FIG. 5). In a directional configuration, as illustrated in FIG. 4, the electrodes 108 only extend a portion of the height 126 of the microelectrode film 104. For example, in a directional configuration the electrodes 108 may each only extend between about 10% and about 80%, between about 10% and about 60%, between about 10% and about 40%, or between about 10% and about 25% of the height 126 of the body 120. The electrodes 108 can be grouped in column to span the height 126. One or more of the directionally configured electrodes 108 can be electrically coupled together to form an omnidirectional electrode 108. The coupling between at least two directionally configured electrodes 108 to form an omnidirectional electrode 108 can occur electrically by connecting two traces 124 within microelectrode film 104 or by connecting terminal contacts 116 via the wires 106.

The microelectrode film 104 can include a plurality of traces 124. The traces 124 can couple the electrodes 108 with one or more contacts 118. The microelectrode film 104 can include the same number of contacts 118 and electrodes 108 such that each electrode 108 is coupled with a single contact 118. The microelectrode film 104 can include fewer contacts 118 than electrodes 108, such that more than one electrode 108 is coupled with the same contact 118 (to form, for example, an omnidirectional electrode). Each trace 124 can make one or more connections with an electrode 108. For example, a trace 124 can branch into two or more periphery traces that couple with the electrode 108 at couple with the electrode 108 at several points around the periphery of the electrode 108. Making multiple connections with each of the electrodes 108 can increase the reliability of the microelectrode film 104.

The extension 122 can include the contacts 118. The contacts 118 can provide an interface where the wires 106 are coupled with the microelectrode film 104. For example, each of the wire 106 can be wire bonded or laser bonded with a respective one of the contacts 118.

The extension 122 can include a first leg 128 and a second leg 130. The contacts 118 can be disposed on a first face of the first leg 128. The first leg 128 can also include an opening 158 disposed toward each end of the first leg 128. The openings 158 can be holes through the first leg 128. The openings 158 can align with inlets that are formed in the attachment face of the support comb 102 (and described further below in relation to FIG. 8, among others). The second leg 130 can include a subset of the traces 124 that run from the contacts 118 to the electrodes 108. Running the subset of the traces 124 along the second leg 130 can enable a greater number of traces 124 (and therefore electrodes 108) to be incorporated into the microelectrode film 104 when compared to a system that routes the traces 124 along a single leg.

FIG. 5 illustrates the microelectrode film 104 in the rolled configuration. As illustrated, opposite edges of the body 120 are rolled toward one another to form a cylinder. The second leg 130 is rolled about the first leg 128 to form a second portion of the cylinder. As described in relation to FIGS. 5 and 6, among others, the body 120 can be rolled about a support tube.

Figure 6:
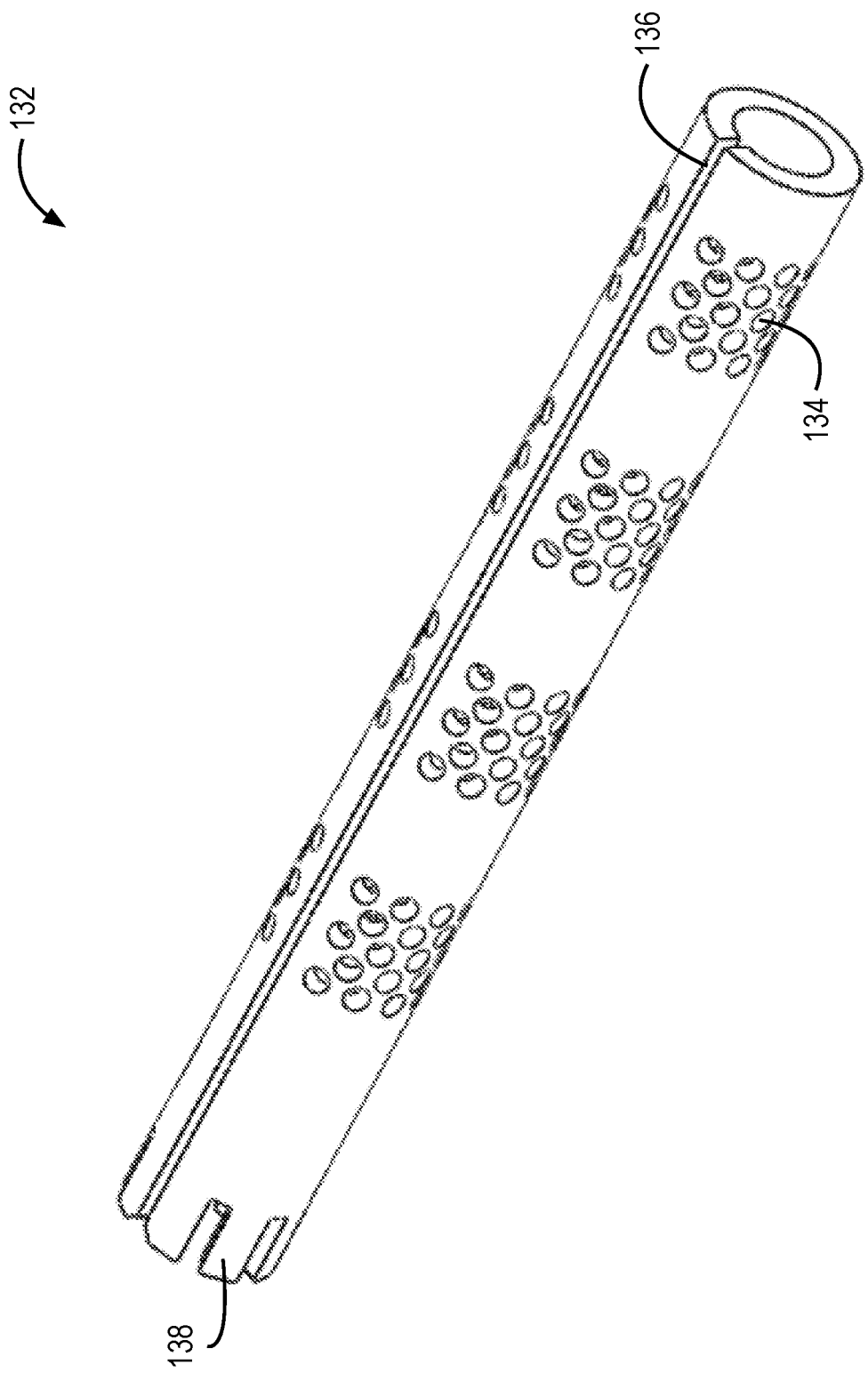
FIG. 6 illustrates an example support tube for use in the stimulation lead illustrated in FIG. 2.

FIG. 6 illustrates an example support tube 132. The support tube 132 can include a plurality of markers 134. The support tube 132 can include a slot 136. The proximal end of the support tube 132 can include a plurality of merlons 138.

The support tube 132 can include a radio opaque metal, such as a medical grade stainless steel, non-metal materials, such as plastic, or a combination thereof. The support tube 132 can include a plurality of markers 134. The markers 134 can be radio opaque. For example, the markers 134 can be visible when the stimulation lead 100 is imaged with a CT scanner or x-ray. When the support tube 132 is manufactured from a radio opaque metal, the markers 134 can be holes or voids in the body of the support tube 132. The markers 134 can pass through the wall of the support tube 132. When the markers 134 are holes through the wall of the support tube 132, the regions without the markers 134 can be relatively more radio opaque when compared to the portions of the support tube 132 with the markers 134. The electrodes 108 can be aligned with the markers 134. The electrodes 108 can be aligned with the regions between the markers 134. The support tube 132 can be manufactured in a plastic material and the markers 134 can be made radio opaque by either, a localized doping of the polymer such as Boron bombardment or by backfilling with a doped polymer for example Boron doped plastic.

The support tube 132 can include a plurality of merlons 138. The merlons 138 can be a plurality of extensions that extend from one end of the support tube 132. Each merlon 138 can be separated from a neighboring merlon 138 by a gap or crenel. Each of the merlons 138 can be about between about 0.2 mm and about 2 mm, between about 0.4 mm and about 1.5 mm, between about 0.2 mm and about 1 mm, or between about 0.4 mm and about 0.6 mm long. The merlons 138 can have a circumferential pitch of about 0.1 mm to about 2 mm, between about 0.1 mm and about 1.5 mm, between about 0.1 mm and about 1 mm, between about 0.1 mm and about 0.5 mm, or between about 0.2 mm and about 4 mm.

The merlons 138 are configured to mate with the support comb 102. The merlons 138 are configured to mate with the probe shaft of the stimulation lead 100. The probe shaft can be formed by an epoxy over-molding process. The merlons 138 can provide groves and ridged to into which the epoxy can flow and bond to form the probe shaft.

The support tube 132 can include a slot 136. The slot 136 can run the length of the support tube 132. The slot 136 can pass through the wall of the support tube 132 or can form a channel in the outer face of the support tube 132.

Figure 7:
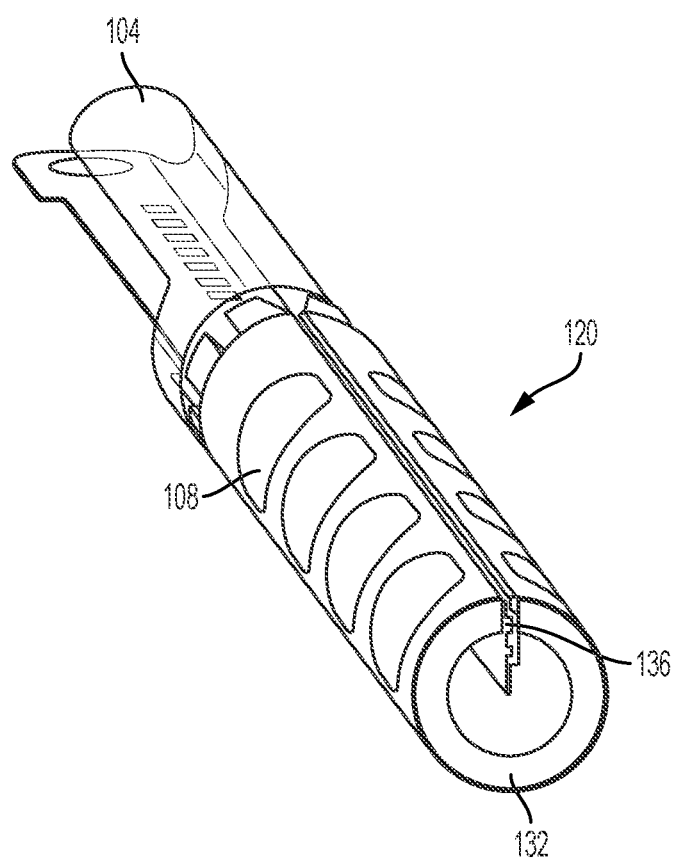
FIG. 7 illustrates the microelectrode film coupled with the support tube, as viewed from the distal end of the support tube.

FIG. 7 illustrates the microelectrode film 104 coupled with the support tube 132, as viewed from the distal end of the support tube 132. A first face of the body 120, which includes the electrodes 108 can faces outward and away from the support tube 132. A second face of the microelectrode film's body 120 is coupled with the external face of the support tube 132 to form a cylinder. The opposing edges of the body 120 are inserted through the slot 136.

Figure 8:
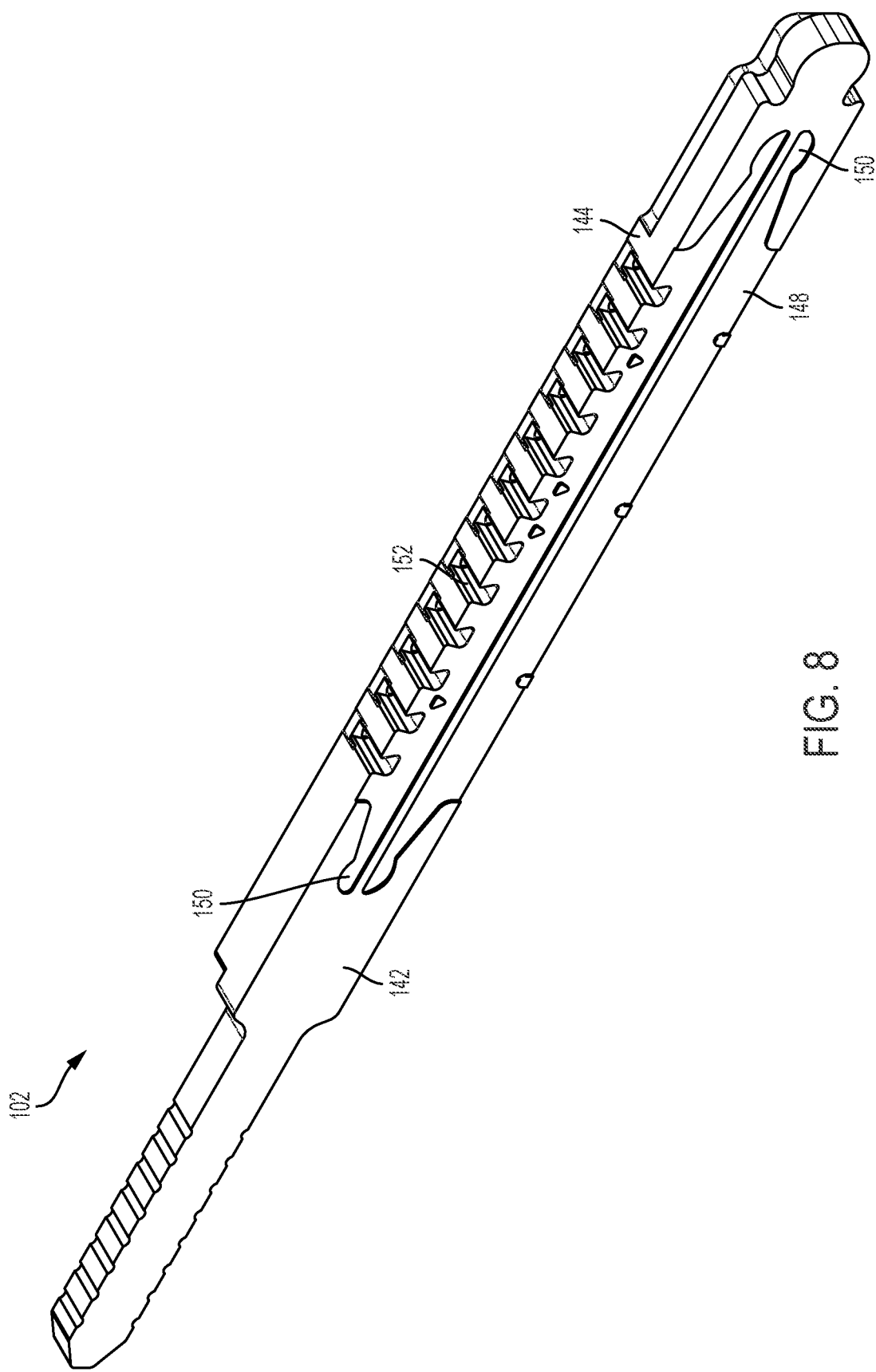
FIGS. 8-10 illustrate an example support comb for use in the stimulation lead illustrated in FIG. 2.

FIG. 8 illustrates an attachment face of the support comb 102 and a first routing face 144 of the support comb 102. The attachment face 142 includes a channel 148. The attachment face 142 of the support comb 102 is configured to couple with a face of the microelectrode film 104. The channel 148 is configured to route an adhesive under a portion of face of the microelectrode film 104 that is coupled with the attachment face 142. The channel 148 can be between about 5 µm and about 40 µm, between about 10 µm and about 30 µm, or between about 10 µm and about 20 µm. During the manufacturing of the stimulation lead 100, a face of the microelectrode film 104 can be coupled with the attachment face 142 of the support comb 102 through a mechanical means, such as a clamp. The inlets 150 can extend past the portion of the microelectrode film 104 that is coupled with the attachment face 142. An adhesive can be added to the inlets 150. Capillary action can transport the adhesive along the length of the channel 148 and under the face of the microelectrode film 104 that is coupled with the attachment face 142. Once the adhesive sets, the mechanical means for holding the microelectrode film 104 against the attachment face 142 can be released.

The support comb 102 can include a first routing face 144. The first routing face 144 can include plurality of slots 152 (which can also be referred to as channels 152). The first routing face 144 can include a slot 152 for each of the wires 106. During the manufacturing process, each of the contacts 118 can be substantially aligned with one of the slots 152 to facilitate coupling the wires 106 with contacts 118. For example, each of the wires 106 can pass through a respective slot 152 to align with a different contact 118. The pitch of the slots 152 can match the pitch of the contacts 118.

Figure 9:
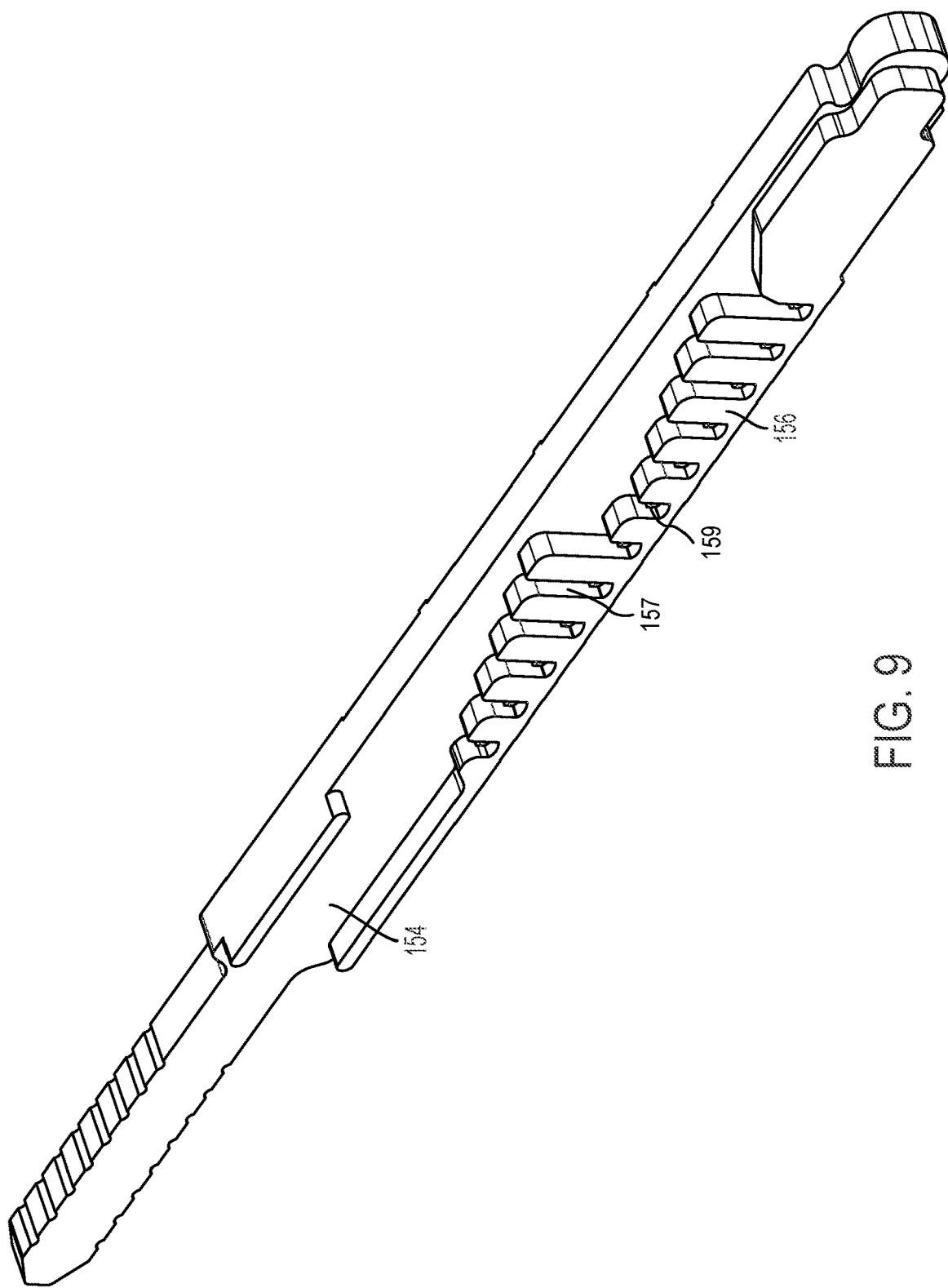

FIG. 9 illustrates a second routing face 154 of the support comb 102. The second routing face 154 is opposite the attachment face 142. The second routing face 154 can include a plurality of fingers 156. The fingers 156 are raised protrusions that can form channels 157 in the second routing face 154. Each of the channels 157 can terminate in a hole 159 that passed to the slots 152 on the first routing face 144.

Figure 10:
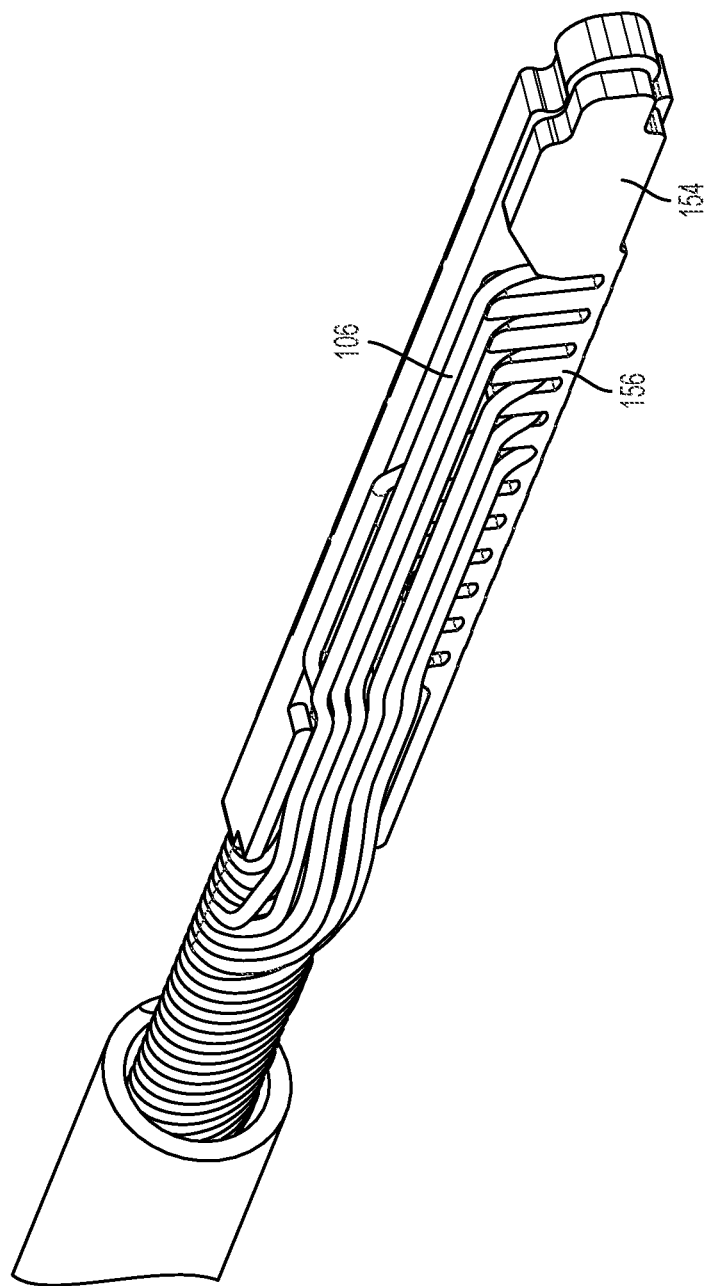
Figure 11:
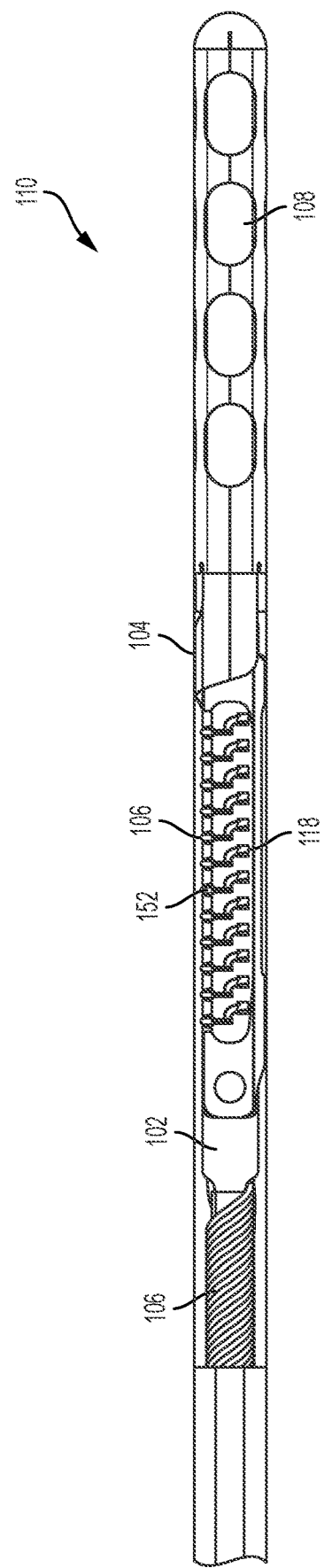
FIGS. 11-14 illustrate views of the distal end of the stimulation lead illustrated in FIG. 2.
Figure 12:
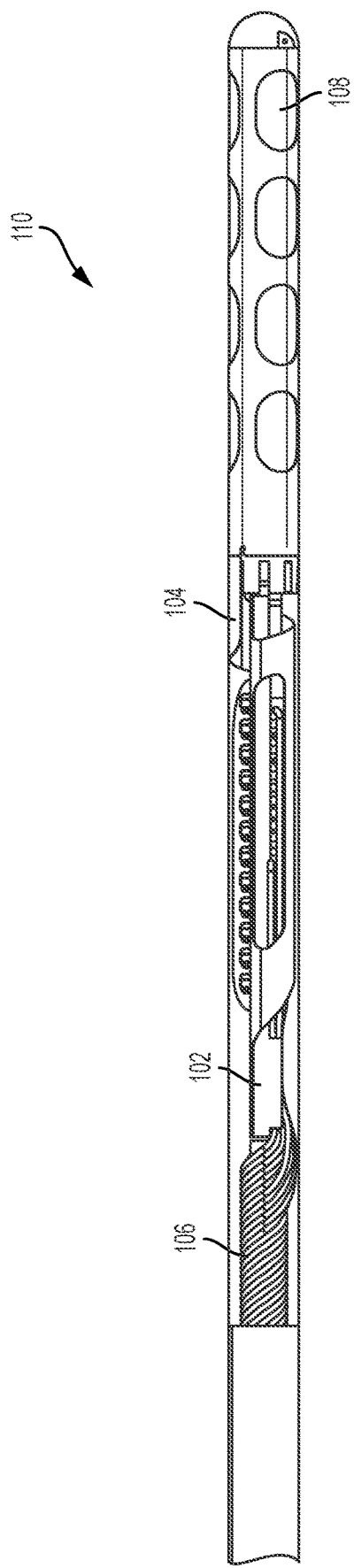
Figure 13:
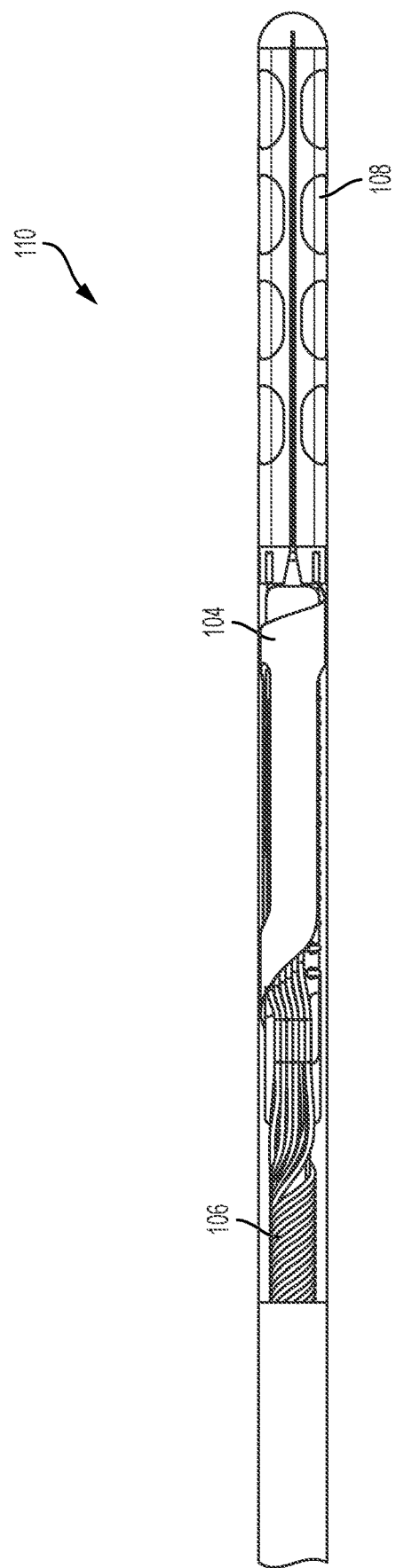
Figure 14:
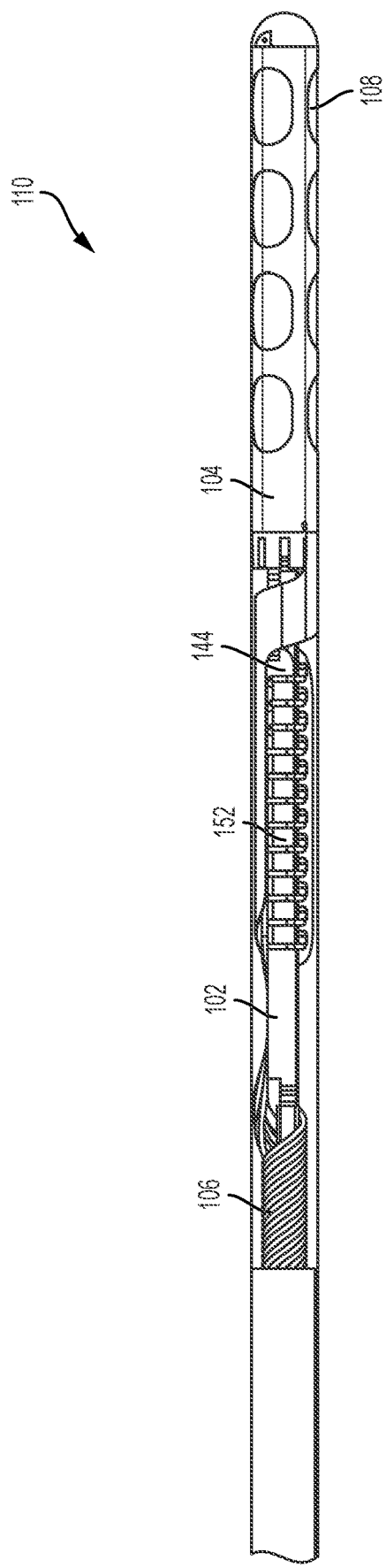

FIG. 10 illustrates the second routing face 154 with wires 106 passing along the second routing face 154. The wires 106 can pass into the channels 157 defined by the fingers 156. From the channels 157, the wires 106 can pass through the hole 159 at the end of the channel 157 and into one of the respective slots 152 on the first routing face 144. The color coding of the wires 106 can enable the appropriate routing of wires 106 from each one of the terminal contacts 116 to the corresponding electrodes 108 of the distal end 110.

FIGS. 11-14 illustrate different face views of the distal end 110. Each of the views illustrated in FIGS. 11-14 illustrate a view of the distal end 110 of the stimulation lead 100 rotated 90 degrees with respect to the previous FIG. For example, FIG. 11 can be said to illustrate a top view of the distal end 110, FIG. 12 can be said to illustrate a first side view of the distal end 110, FIG. 13 can be said to illustrate a bottom view of the distal end 110, and FIG. 14 can be said to illustrate a second side view of the distal end 110. The preceding "top", "first side," "second side," and "bottom" are provided for reference only as any face of the distal end 110 can serve as the "top," "bottom," etc. For example, the placement of the electrodes 108 around the circumference of the distal end 110 enable any face (or angle) of the distal end 110 to serve as the top, bottom, or side of the distal end 110.

Referring to FIGS. 11-14 together, among others, the distal end 110 includes the microelectrode film 104. The microelectrode film 104 includes a plurality of electrodes 108. The electrodes 108 are coupled with the terminal contacts 116 via the wires 106. The distal end 110 also includes the support comb 102. The support comb 102 can facilitate the management of the wires 106 within the shaft of the distal end 110. The support comb 102 can also secure or hold the terminating ends of the wires 106 near the contacts of the microelectrode film 104. Positing the terminating ends of the wires 106 near the contacts of the microelectrode film 104 can enable for improved efficiencies in manufacturing as the support comb 102 can provide alignment between the wires 106 and the contacts 118 of the microelectrode film 104.

Figure 15:
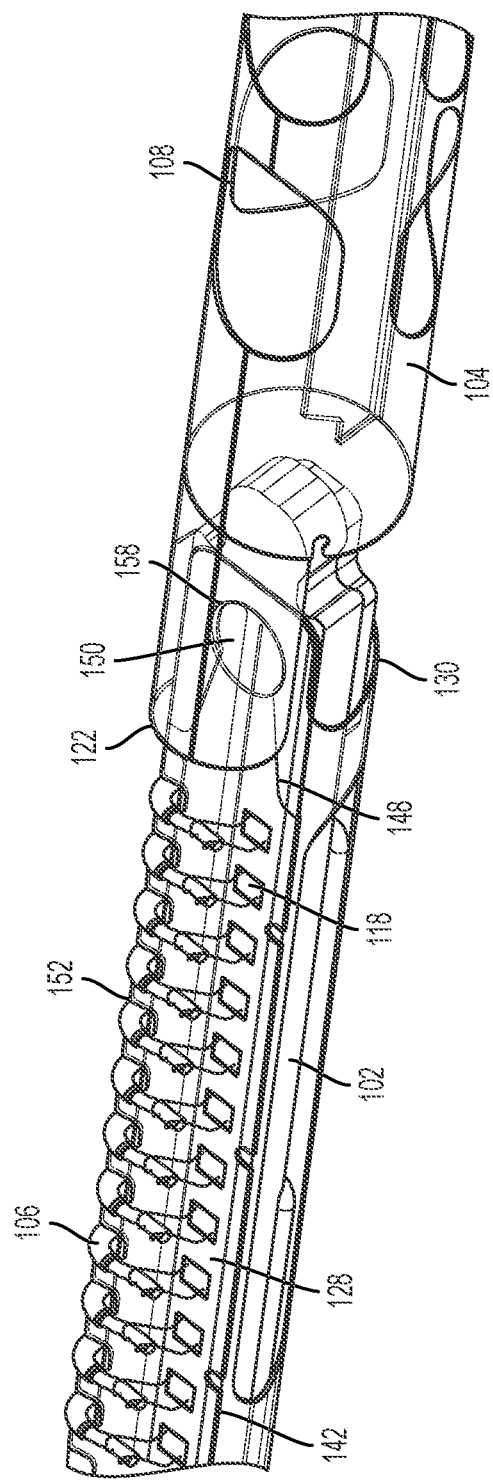
FIG. 15 illustrates a partial view of the interface between the support comb and the microelectrode film in the stimulation lead illustrated in FIG. 2.

FIG. 15 illustrates an enlarged view of the interface between the support comb 102 and the microelectrode film 104. FIG. 15 illustrates the microelectrode film 104 in the rolled or cylindrical configuration. The extension 122 of the microelectrode film 104 is rolled around the support comb 102 such that support comb 102 is positioned within a lumen defined by the rolled (or cylindrical) microelectrode film 104. The second leg 130 is wrapped around the support comb 102 and positioned toward the support comb's second routing face 154 (illustrated in FIG. 15 as the backside of the support comb 102). The first leg 128 can be coupled with the attachment face 142.

The first leg 128 of the microelectrode film 104 can be coupled with the attachment face 142. The first leg 128 can include a first face that includes the contacts 118 and a second face, opposite the first face, that can couple with the support comb 102. The second face can be coupled with the attachment face 142. The first leg 128 can be positioned on the attachment face 142 such that the opening 158 substantially aligns with the inlet 150. For example, before rolling the extension 122 around the support comb 102, an adhesive can be delivered to the inlet 150 through the opening 158 in the first leg 128. Through capillary action, the adhesive can flow through the channel 148 and under the first leg 128 to couples the first leg 128 (e.g., the second face of the first leg 128) with the attachment face 142.

Coupling the first leg 128 with the attachment face 142, the contacts 118 can be substantially aligned with the slots 152. The contacts 118 can be offset from the slots 152. For example, each of the contacts 118 can be positioned between neighboring slots 152. The slots 152 can enable wire management and position the wires 106 in a correct position for bonding with the contacts 118. For example, the wires 106 can pass through each of the slots 152 to align with one of the contacts 118. The wires 106 can be coupled with the contacts 118. The wires 106 can be wire bonded or welded with the contacts 118.

Figure 16:
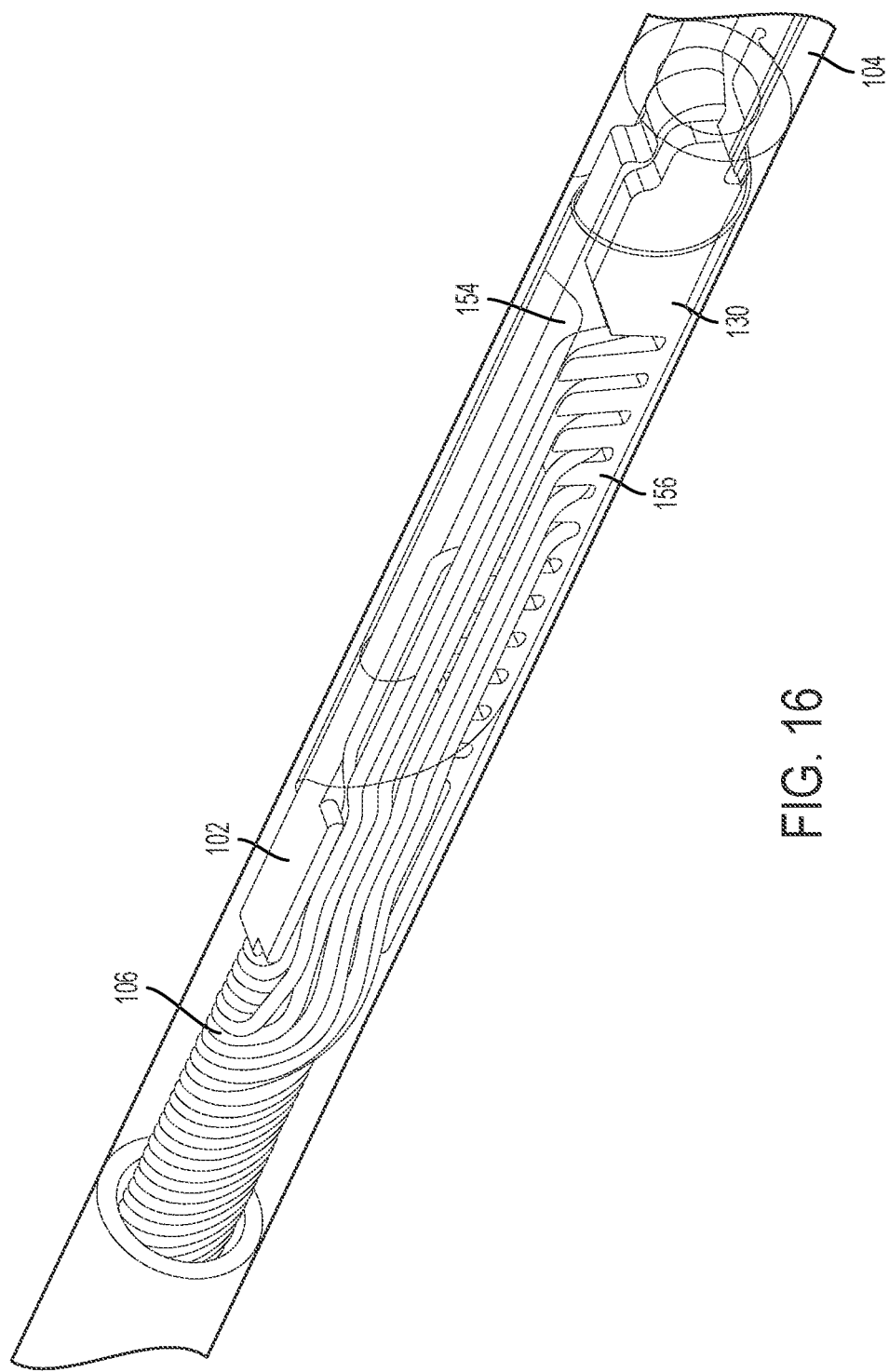
FIG. 16 illustrates a partial view of an example support comb that can be used in the stimulation lead illustrated in FIG. 2.

FIG. 16 illustrates an enlarged view of the support comb 102. FIG. 16 substantially illustrates the back side of the support comb 102 (and distal end 110) with respect to FIG. 15.

As illustrated, the second leg 130 of the microelectrode film 104 is rolled around the support comb 102. The wires 106 pass along the second routing face 154 of the support comb 102. Each of the wires 106 pass through a channel formed by the fingers 156. The wires 106 can pass through a hole 159 formed at the end of the channel 157 and into the slots 152. The fingers 156 (and the channels formed thereby) can enable routing of the wires 106 along the support comb 102 and to the slots 152 where the wires 106 can be coupled with the contacts 118.

Figure 17:
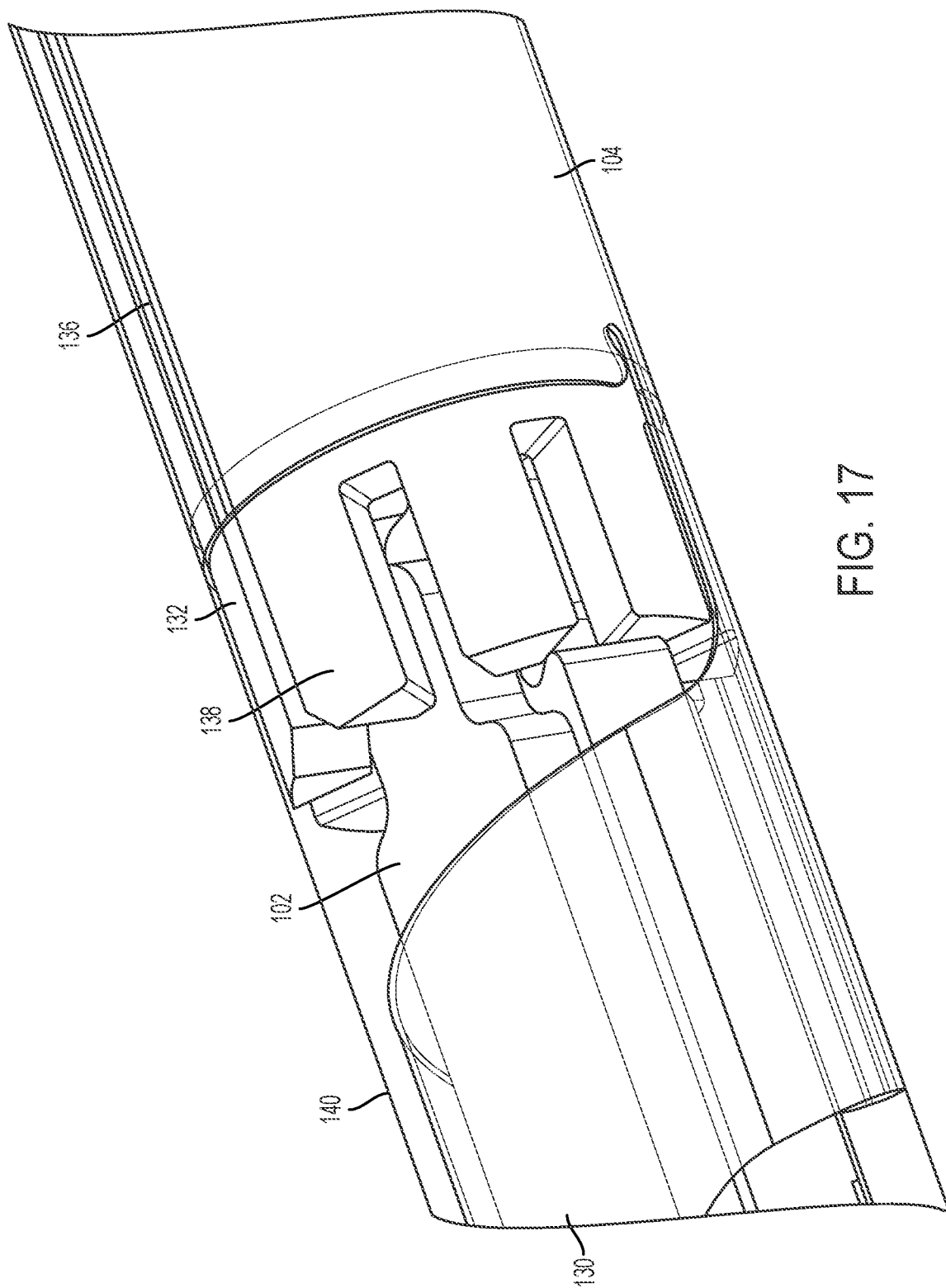
FIG. 17 illustrates a partial view of the coupling of the support comb with the support tube.

FIG. 17 illustrates an enlarged view of the coupling of the support comb 102 with the support tube 132. A first end of the support comb 102 can include a knob or other structure that is configured to fit within a portion of the support tube 132. The merlons 138 can surround the knob at the first end of the support comb 102. The probe shaft 140 can be formed through an epoxy over molding process. The epoxy can flow into the areas between the merlons 138 to form a probe shaft 140 that is coupled with the support tube 132. The epoxy of the probe shaft 140 can encase the support comb 102 and the second leg 130 within the body of stimulation lead's distal end 110. The probe shaft 140 can be formed from an injection molding or micromachining process.

Figure 18:
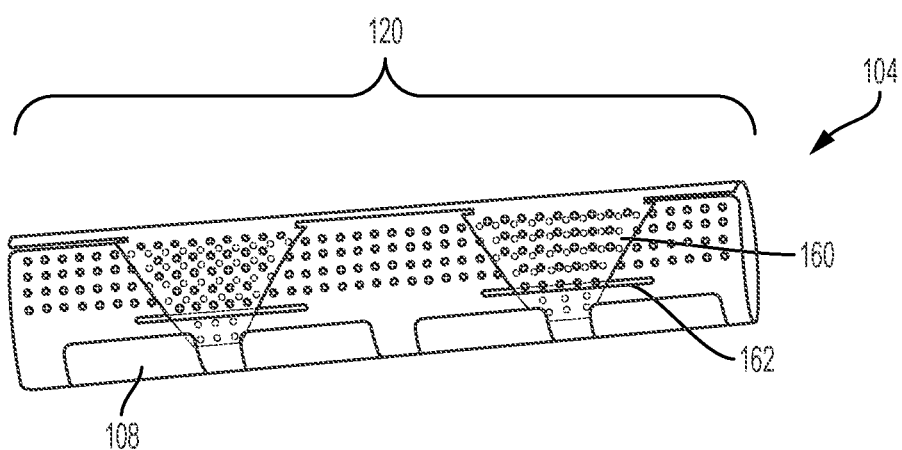
FIGS. 18 and 19 illustrate example configurations of the microelectrode film with tabs.
Figure 19:
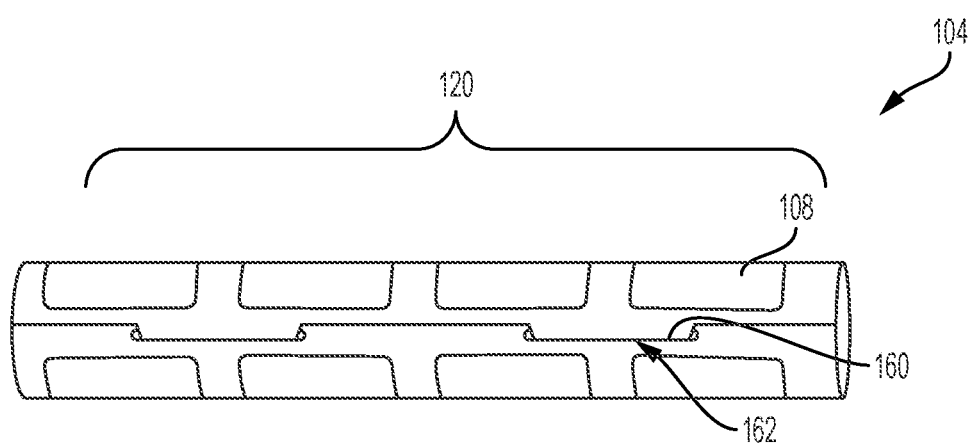

FIGS. 18 and 19 illustrate an example configuration of the microelectrode film 104 and method for forming the microelectrode film 104 into a cylinder. FIG. 19 illustrates the body 120 portion of the microelectrode film 104 in a partially rolled state. A first edge of the body 120 can include a plurality of tabs 160. The opposite edge (or towards the opposite edge) can include a plurality of slots 162. The body 120 can include a slot 162 for each of the tab 160. The tabs 160 can be tapered—narrowing as the tab 160 extends from the body 120. For example, the tabs 160 can be shaped like the head of an arrow. Each of the tabs 160 can slide into a respective one of the slots 162. The tabs 160 can include a barb that locks the tab 160 into the slot 162 once the tab 160 is inserted into the slot 162 past the barb. FIG. 19 illustrates the body 120 with the tabs 160 fully inserted into the slots 162 to form a cylinder.

Figure 20:
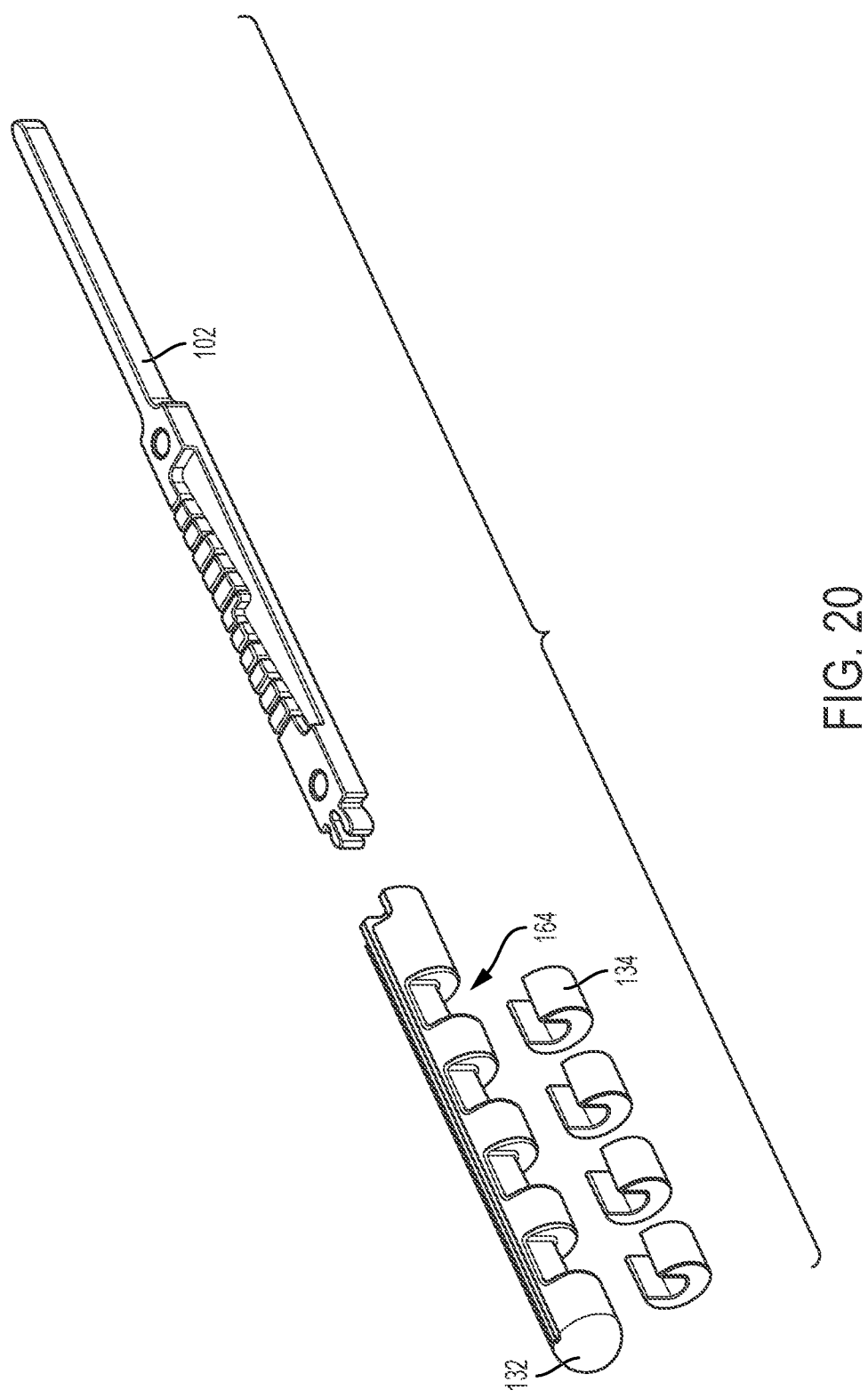
FIG. 20 illustrates an example support tube and markers for use in the system illustrated in FIG. 1.

FIG. 20 illustrates an example support tube 132 and markers 134. The example support tube 132 illustrated in FIG. 20 can be manufactured from a non-magnetic or non-radio opaque material. The markers 134 can be manufactured from a radio opaque material. The support tube 132 can include a plurality of grooves 164. The grooves 164 can be shaped to receive the markers 134. The markers 134 can be secured into the grooves 164 with an adhesive, clip, or pressure fitting. When the microelectrode film 104 is coupled with the support tube 132, the electrodes 108 can be aligned with the markers 134.

Figure 21:
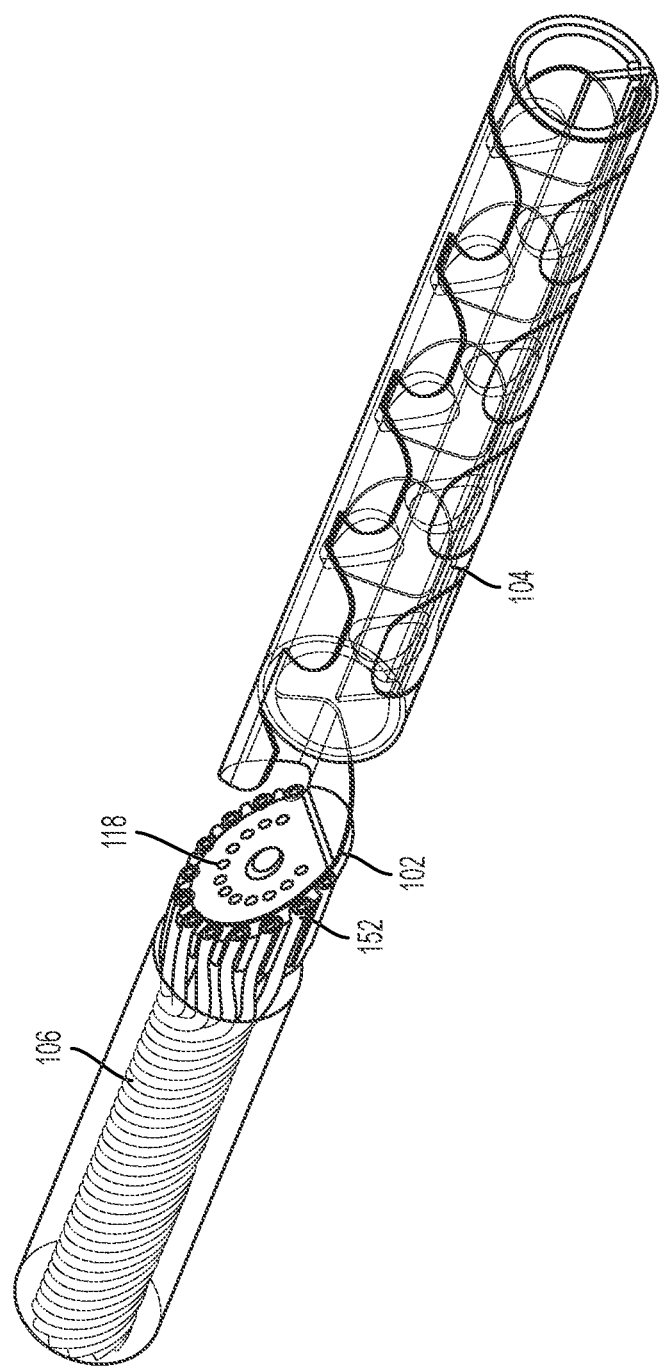
FIG. 21 illustrates an example support comb with a circular configuration for use in the system illustrated in FIG. 1.

FIG. 21 illustrates an example support comb 102 in a circular configuration. The support comb 102 can include a plurality of slots 152 around the circumference of the support comb 102. The extension of the microelectrode film 104 can be disk shaped and can include a plurality of contacts 118 distributed toward the circumference of the extension. The wires 106 can pass through each of the slots 152 toward the contacts 118. The slots 152 can align the wires 106 with the contacts 118. The wires 106 can be wire bonded or welded to the contacts 118.

Figure 22:
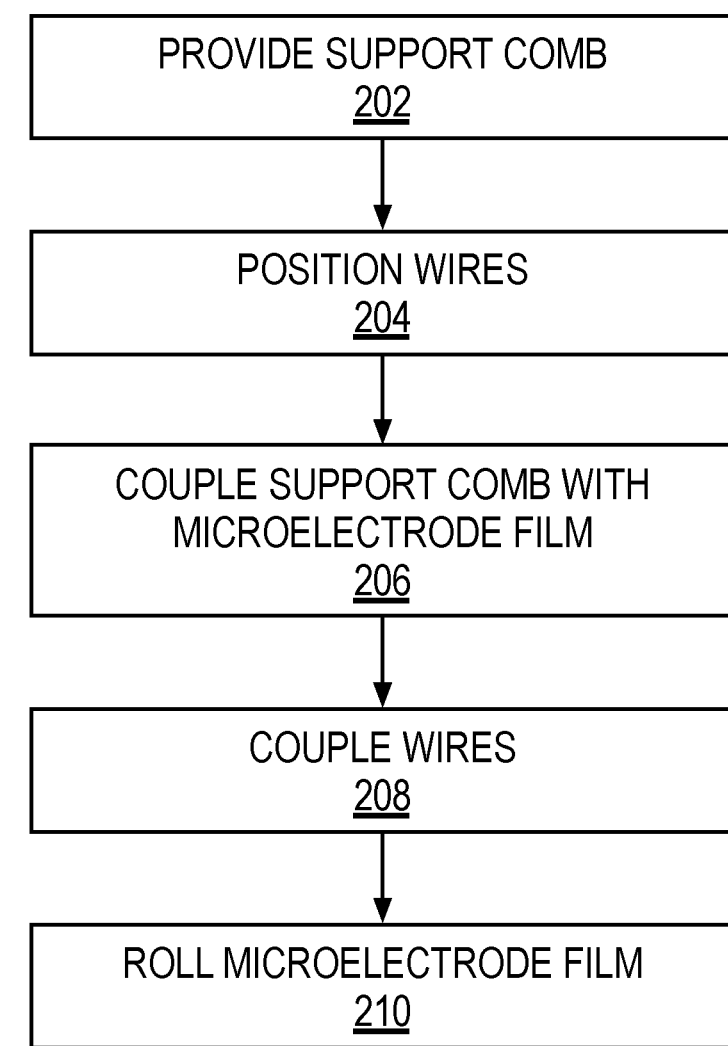
FIG. 22 illustrates an example method to manufacture the lead device for use in the system illustrated in FIG. 1.

FIG. 22 illustrates an example method 200 to manufacture a lead device. The method 200 can include providing a support comb (BLOCK 202). The method 200 can include positioning a plurality of wires (BLOCK 204). The method 200 can include coupling the support comb with a microelectrode film (BLOCK 206). The method 200 can include coupling the wires with the microelectrode film (BLOCK 208). The method 200 can include rolling the microelectrode film (BLOCK 210).

As set forth above, the method 200 can include providing a support comb (BLOCK 202). Referring also to FIGS. 1-21, the support comb 102 can include an attachment face 142 and first routing face 144. The first routing face 144 can include a plurality of slots 152. The microelectrode film 104 can include a second routing face 154. The second routing face 154 can include a plurality of fingers 156 that form channels on the second routing face 154. The channels 157 can terminate in a hole 159 that connects the channels 157 of the second routing face 154 with the slots 152 of the first routing face 144. The attachment face 142 can include a channel 148.

The support comb 102 can be manufactured by an injection molding process, a micromachining process, a photolithography process, or 3D-printing process. The support comb 102 can be manufactured from silicon, plastic, metal, liquid crystal polymers (LCP), or other material. Radio opaque materials can include included into the support comb 102 to enable the distal end 110 to be visualized during an X-ray. For example, the polymers used in an injection molding process can be doped with a radio opaque material such as Barium Sulfate (BaSO4), Boron, or metal rings, bands, or components can be incorporated into the support comb 102.

The method 200 can include positioning the wires (BLOCK 204). Referring to FIG. 10, among others, the wires 106 can uncoil and run along the second routing face 154. The second routing face 154 can arrange the wires 106. The second routing face 154 can include a plurality of fingers 156 that can define channels 157. A wire 106 can pass through a respective channel 157 and through a hole 159 at the end of the channel 157 that couples the channel 157 with a slot 152. Each of the wires 106 can pass through a respective one of the slots 152. The slots 152 can hold and position the wires 106. For example, the slots 152 can hold each of the wires 106 in a fixed proximity to a respective contact 118.

The method 200 can include coupling the support comb 102 with a microelectrode film 104 (BLOCK 206). The microelectrode film 104 can include different portions. For example, the microelectrode film 104 can include a body 120 and an extension 122. The body 120 can include a plurality of electrodes 108. The extension 122 can include a plurality of legs. One of the legs can include a plurality of contacts 118. Both the extension 122 and the body 120 can include a plurality of traces 124.

The microelectrode film 104 can include a stack of insulating and conducting layers. The microelectrode film can be a thin-film, microelectromechanical systems (MEMS) electrode film. The conducting layers can include the traces 124, the contacts 118, and the electrodes 108. The different conducting layers can be isolated from one another by the insulating layers. The insulating layers can also isolate the conducting layers (or portions thereof) from the external environment. The microelectrode film 104 can be manufactured as a planar film using additive manufacturing processes.

The microelectrode film 104 can be coupled with the support comb 102 by coupling a first portion of the microelectrode film 104 with the attachment face 142. For example, a portion of the extension 122 can be coupled with the attachment face 142. The first leg 128 of the extension 122, which can include a plurality of contacts 118 can be coupled with the attachment face 142. The face opposite the face with the contacts 118 can be coupled with the attachment face 142 such that the contacts 118 faces away from the support comb 102.

When coupling the microelectrode film 104 with the support comb 102, the openings 158 of the extension 122 can be aligned with the inlets 150 of the support comb 102. The microelectrode film 104 can be coupled with the support comb 102 by applying an adhesive to the inlets 150. Capillary force can drive the adhesive from the inlets 150 and through the channel 148 to underfill the space between the microelectrode film 104 and the support comb 102 formed by the channel 148. Once cured, the adhesive can couple the microelectrode film 104 with the support comb 102.

The method 200 can include coupling the wires with the microelectrode film (BLOCK 208). Also, Referring to FIG. 15, among others, the wires 106 can pass through a respective channel on the second routing face 154 and into a respective slot 152. The slot 152 can position each of the wires 106 near one of the contacts 118. The wires 106 can be coupled with the contacts 118 with wire bonding, welding, or laser bonding.

The method 200 can include rolling the microelectrode film (BLOCK 210). The extension 122 of the microelectrode film 104 can be rolled about the support comb 102. The body 120 of the microelectrode film 104 can be rolled about the support comb 102. Rolling the extension 122 about the support comb 102 can place the second leg 130 of the extension 122 near the second routing face 154 of the support comb 102.

The body 120 of the microelectrode film 104 can be rolled about the support tube 132. The microelectrode film 104 can be coupled with the outer face of the support tube 132. The support tube 132 can include a slot 136. Opposite edges of the body 120 can be inserted into the slot 136.

Once the microelectrode film 104 is rolled, the microelectrode film 104 and support comb 102 can be placed in a mold. The mold can be filled with an epoxy. The epoxy over molding can form a probe shaft 140. The probe shaft 140 can encase the extension 122, the support comb 102, and at least a portion of the wires 106. The probe shaft 140 can flow into the merlons 138 and couples with the support tube 132.

While operations are depicted in the drawings in a particular order, such operations are not required to be performed in the particular order shown or in sequential order, and all illustrated operations are not required to be performed. Actions described herein can be performed in a different order.

The separation of various system components does not require separation in all implementations, and the described program components can be included in a single hardware or software product.

Having now described some illustrative implementations, it is apparent that the foregoing is illustrative and not limiting, having been presented by way of example. In particular, although many of the examples presented herein involve specific combinations of method acts or system elements, those acts and those elements may be combined in other ways to accomplish the same objectives. Acts, elements and features discussed in connection with one implementation are not intended to be excluded from a similar role in other implementations or implementations.

The phraseology and terminology used herein is for the purpose of description and should not be regarded as limiting. The use of "including" "comprising" "having" "containing" "involving" "characterized by" "characterized in that" and variations thereof herein, is meant to encompass the items listed thereafter, equivalents thereof, and additional items, as well as alternate implementations consisting of the items listed thereafter exclusively. In one implementation, the systems and methods described herein consist of one, each combination of more than one, or all of the described elements, acts, or components.

As used herein, the term "about" and "substantially" will be understood by persons of ordinary skill in the art and will vary to some extent depending upon the context in which it is used. If there are uses of the term which are not clear to persons of ordinary skill in the art given the context in which it is used, "about" will mean up to plus or minus 10% of the particular term.

Any references to implementations or elements or acts of the systems and methods herein referred to in the singular may also embrace implementations including a plurality of these elements, and any references in plural to any implementation or element or act herein may also embrace implementations including only a single element. References in the singular or plural form are not intended to limit the presently disclosed systems or methods, their components, acts, or elements to single or plural configurations. References to any act or element being based on any information, act or element may include implementations where the act or element is based at least in part on any information, act, or element.

Any implementation disclosed herein may be combined with any other implementation or embodiment, and references to "an implementation," "some implementations," "one implementation" or the like are not necessarily mutually exclusive and are intended to indicate that a particular feature, structure, or characteristic described in connection with the implementation may be included in at least one implementation or embodiment. Such terms as used herein are not necessarily all referring to the same implementation. Any implementation may be combined with any other implementation, inclusively or exclusively, in any manner consistent with the aspects and implementations disclosed herein.

The indefinite articles "a" and "an," as used herein in the specification and in the claims, unless clearly indicated to the contrary, should be understood to mean "at least one."

References to "or" may be construed as inclusive so that any terms described using "or" may indicate any of a single, more than one, and all of the described terms. For example, a reference to "at least one of 'A' and 'B'" can include only 'A', only 'B', as well as both 'A' and 'B'. Such references used in conjunction with "comprising" or other open terminology can include additional items.

Where technical features in the drawings, detailed description or any claim are followed by reference signs, the reference signs have been included to increase the intelligibility of the drawings, detailed description, and claims. Accordingly, neither the reference signs nor their absence have any limiting effect on the scope of any claim elements.

The systems and methods described herein may be embodied in other specific forms without departing from the characteristics thereof. The foregoing implementations are illustrative rather than limiting of the described systems and methods. Scope of the systems and methods described herein is thus indicated by the appended claims, rather than the foregoing description, and changes that come within the meaning and range of equivalency of the claims are embraced therein.

What is claimed is:

1. An implantable lead device, comprising:
   a support comb comprising:
      an attachment face; and
      a routing face comprising a plurality of slots;
   a microelectrode film comprising a body having a plurality of electrodes and an extension comprising:
      a first leg, the first leg of the extension having a plurality of electrical contacts coupled with the plurality of electrodes; and
      a second leg, the second leg of the extension coupled with the attachment face of the support comb; and
      a plurality of wires, each of the plurality of wires passing through a respective one of the plurality of slots and coupled with a respective one of the plurality of electrical contacts.

2. The lead of claim 1, wherein the attachment face comprises a channel to route an adhesive under at least a portion of the second leg of the microelectrode film.

3. The lead of claim 1, comprising:
   a support tube; and
   a face of the body of the microelectrode film coupled with the support tube.

4. The lead of claim 3, wherein the support tube comprises a plurality of radio opaque markers aligned with the plurality of electrodes.

5. The lead of claim 3, wherein the support tube comprises a plurality of merlons on a first end, the first end configured to mate with the support comb.

6. The lead of claim 1, comprising:
   a support tube comprising a plurality of radio opaque markers.

7. The lead of claim 1, wherein each of the plurality of wires are coupled with the respective one of the plurality of electrical contacts with wire bonding.

8. The lead of claim 1, wherein the extension of the microelectrode film comprises:
   the first leg comprising the first face of the extension and the second face of the extension; and
   the second leg comprising a plurality of traces coupling a subset of the plurality of electrodes to the plurality of electrical contacts.

9. The lead of claim 1, wherein the extension of the microelectrode film comprises:
   the first leg and the second leg rolled around the support comb.

10. The lead of claim 1, comprising:
    an epoxy backfilling the microelectrode film.

11. A method, comprising:
    providing a support comb of an implantable lead device, the support comb comprising:
       an attachment face; and
       a routing face comprising a plurality of slots;
    coupling a first leg of a microelectrode film of the implantable lead device with the attachment face of the support comb, the first leg of the microelectrode film comprising a plurality of electrical contacts;
    positioning each of a plurality of wires through a respective one of the plurality of slots of the routing face;
    coupling each of the plurality of wires with a respective one of the plurality of electrical contacts; and
    rolling a second leg of the microelectrode film about the support comb.

12. The method of claim 11, comprising:
    forming the second leg of the microelectrode film comprising a plurality of electrodes in electrical communication with the plurality of electrical contacts; and
    forming a third leg of the microelectrode film comprising a plurality of electrical traces coupling a portion of the plurality of electrodes to a portion of the plurality of electrical contacts.

13. The method of claim 11, comprising:
    coupling a second leg of the microelectrode film to an outer face of a support tube, the second leg of the microelectrode film comprising the plurality of electrodes; and
    filling the support tube with an epoxy.

14. The method of claim 11, comprising:
    forming a plurality of radio opaque markers in a support tube; and
    aligning the plurality of radio opaque markers with the plurality of electrodes formed in the microelectrode film.

15. The method of claim 11, comprising:
    wire bonding each of the plurality of wires with the respective one of the plurality of electrical contacts.

16. The method of claim 11, comprising:
rolling the second leg of the microelectrode film to form a cylinder; and
filling the cylinder with an epoxy.
17. The method of claim 11, comprising:
underfilling a channel formed in the attachment face with an epoxy to couple the first leg of the microelectrode film with the attachment face.
18. The method of claim 11, comprising:
etching the support comb in silicon.
19. The method of claim 11, comprising:
coupling a first edge of the microelectrode film with a second edge of the microelectrode film to form a cylinder.
20. The method of claim 11, comprising:
coupling the microelectrode film with a support tube; and
inserting a first edge and a second edge of the microelectrode film into a slot of the support tube.

* * * * *